US010531662B2

(12) United States Patent
Strasburg et al.

(10) Patent No.: US 10,531,662 B2
(45) Date of Patent: Jan. 14, 2020

(54) COMPOUNDS FOR INHIBITION OF FUNGAL MYCOTOXIN AND SPORULATION

(71) Applicants: Board of Trustees of Michigan State University, East Lansing, MI (US); Sokoine University of Agriculture, Morogoro (TZ)

(72) Inventors: Gale M. Strasburg, East Lansing, MI (US); Juma A. Mmongoyo, East Lansing, MI (US); John E. Linz, Lansing, MI (US); Felicia Wu, East Lansing, MI (US); Jovin K. Mugula, Morogoro (TZ); Amila A. Dissanayake, East Lansing, MI (US); Chuan-Rui Zhang, East Lansing, MI (US); Josephine M. Wee, East Lansing, MI (US); Muraleedharan G. Nair, East Lansing, MI (US); Devin M. Day, Grand Ledge, MI (US)

(73) Assignees: Board of Trustees of Michigan State University, East Lansing, MI (US); Sokoine University of Agriculture, Morogoro (TZ)

( * ) Notice: Subject to any disclaimer, the term of this patent is extended or adjusted under 35 U.S.C. 154(b) by 0 days.

(21) Appl. No.: 15/864,696

(22) Filed: Jan. 8, 2018

(65) Prior Publication Data

US 2018/0192648 A1 Jul. 12, 2018

Related U.S. Application Data

(60) Provisional application No. 62/443,998, filed on Jan. 9, 2017.

(51) Int. Cl.
*A01N 43/20* (2006.01)
*A01N 25/02* (2006.01)

(52) U.S. Cl.
CPC ............. *A01N 43/20* (2013.01); *A01N 25/02* (2013.01)

(58) Field of Classification Search
CPC ................................ A01N 43/20; A01N 25/02
See application file for complete search history.

(56) References Cited

PUBLICATIONS

Pradeep Singh Negi, 156 Int'l J. Food Microbiol. 7-17 (2012) (Year: 2012).*

Lajubutu Bolanle Alake, 60 Planta Med. 477 (1994) (Year: 1994).*

* cited by examiner

*Primary Examiner* — Timothy R Rozof

(74) *Attorney, Agent, or Firm* — Schwegman Lundberg & Woessner, P.A.

(57) ABSTRACT

Compounds and compositions are described herein that inhibit the biosynthesis of mycotoxins and fungal sporulation. Such compounds and compositions are useful for inhibiting mold. Methods of using such compounds and compositions are also described herein that involve applying the compositions to plants, plant parts, structures, containers, and other surfaces.

27 Claims, 10 Drawing Sheets

DQ

3HDQ 3000.163US1

Norsolorinic Acid (NA)

Aflatoxins

COMPOUNDS FOR INHIBITION OF FUNGAL MYCOTOXIN AND SPORULATION

CLAIM OF PRIORITY

This application claims benefit of priority to the filing date of U.S. Provisional Application Ser. No. 62/443,998, filed Jan. 9, 2017, the contents of which are specifically incorporated herein by reference in their entity.

FEDERAL FUNDING

This invention was made with government support under CA-621-A-00-11-00009-00 awarded by the U.S. Agency for International Development. The government has certain rights in the invention.

BACKGROUND

Mycotoxins are toxins produced by fungi that contaminate grains and nuts. These toxins cause immunosuppressive, carcinogenic, cytotoxic and teratogenic effects in humans and animals that consume the contaminated grains and nuts. Aflatoxin, the most well-known mycotoxin, is produced by several species of the fungus *Aspergillus* and contaminates corn, tree nuts, cottonseed and peanuts in the southern and western United States. The FDA limits aflatoxin levels in food and feed to 20 ppb, due to its carcinogenic capabilities. Aflatoxin, together with hepatitis C, is associated with high levels of liver cancer in Southeast Asia. Deoxynivalenol, a my cotoxin common in wheat and barley in the Midwest, is produced by several *Fusarium* species on grain crops, has immunosuppressive effects on humans, and induces feed refusal in animals. The FDA suggests levels of less than 15 ppm deoxynivalenol in finished products for human consumption.

Economic losses due to mycotoxins in the United States are estimated to be between $0.5 and $1.5 billion annually. Fungicides are only partially effective against my cotoxigenic fungi because such fungi are naturally tolerant to many fungicides, and because when stressed by fungicide applications, fungi can respond by producing more of the my cotoxin. Durable host plant resistance is not available, despite many y ears of intensive breeding. An alternative to these solutions would be a compound or compounds that block my cotoxin biosynthesis, especially when my cotoxin levels can be high, even in asymptomatic nuts and grains.

SUMMARY

This application describes compounds and compositions that inhibit the biosynthesis of mycotoxins and fungal sporulation. Such compounds and compositions are useful at sites where mold is present or where it may develop. For example, the compounds and compositions described herein are useful as antibiotics.

Compounds and compositions are described herein that can include at least one compound of formula I:

A-linkage-B where:

A and B are bicyclic rings with 8 to 12 ring atoms, each of the A and B bicyclic rings having (i) at least three oxygen-containing substituents selected from hydroxy (—OH), oxy (═O), ether (—O—), and alkoxy (R—OH, where R is a lower alkyl), and (ii) one or two lower alkyl substituents; and linkage is a covalent bond or a lower alkylene (e.g., $—(CH_2)_n—$, where n is an integer of 1-3) bonded to the A and B bicyclic rings.

Specific examples of compounds that can inhibit the biosynthesis of mycotoxins and fungal sporulation include the following:

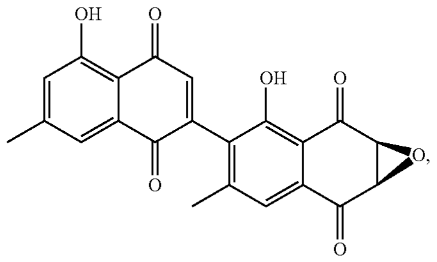

Diosquinone (DQ)

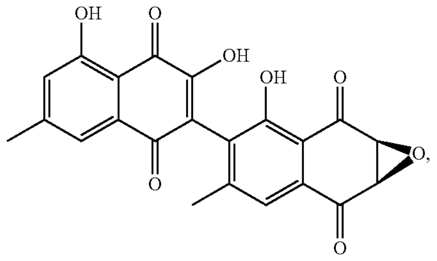

3-Hydroxydiosquinone (3HDQ)

and combinations thereof.

Methods are also described herein that can include applying one or more of the compositions or compounds to one or more plants, one or more plant seeds, one or more plant products, one or more structures, one or more laundry rooms, one or more bathrooms, one or more bedrooms, one or more closets, one or more basements, one or more attics, one or more kitchens, one or more cabinets, one or more animal pens, one or more storage areas, one or more silos, one or more grain bins, one or more building sidings, one or more decks, one or more boat surfaces, or a combination thereof.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A illustrates the inhibitory effects of root powders of *D. mafiensis* on *A. parasiticus* B62 grown on PDA for 3 day s. FIG. 1B illustrates the inhibitory effects of crude methanol extracts of *D. mafiensis* on *A. parasiticus* B62 grown on Potato Dextrose Agar (PDA) for 3 day s. FIG. 1C illustrates the inhibitory effects of sub-fractions E2 and E3 obtained from fraction E on vegetative growth and norsolorinic acid (NA) production by *A. parasiticus* B62. B62 was grown onto GM S in the dark at 30° C. for 5 days. The image was obtained on the fifth day of incubation. Controls: B62 only and B62 with DM SO. Decreases in norsolorinic acid intensity indicates aflatoxin reduction due to the plant extract. Purification of E3 using preparative chromatography afforded two biologically active compounds. FIG. 1D shows structures of two biologically active compounds: diosquinone (DQ) and 3-hydroxy diosquinone (3HDQ).

FIG. 2A illustrates the inhibitory effects of diosquinone (DQ) and 3-hydroxy diosquinone (3HDQ) on *Aspergillus flavus* vegetative growth. FIG. 2B illustrates the inhibitory effects of diosquinone (DQ) and 3-hydroxy diosquinone (3HDQ) on *Aspergillus parasiticus* vegetative growth. FIG. 2C illustrates the inhibitory effects of diosquinone (DQ) and 3-hydroxy diosquinone (3HDQ) on *Aspergillus flavus* sporulation. FIG. 2D illustrates the inhibitory effects of diosquinone (DQ) and 3-hydroxy diosquinone (3HDQ) on *Aspergillus parasiticus* sporulation. FIG. 2E illustrates the inhibitory effects of diosquinone (DQ) and 3-hydroxy diosquinone (3HDQ) on *Aspergillus flavus* total aflatoxin production. FIG. 2F illustrates the inhibitory effects of diosquinone (DQ) and 3-hydroxy diosquinone (3HDQ) on *Aspergillus parasiticus* total aflatoxin production. Differences in data with the same letters are not statistically significant ($p<0.05$) according to Duncan's method of pairwise comparisons tests.

FIG. 3A shows the anthraquinone moiety of norsolorinic acid (red-highlighted) that may mimic the quinone moiety of DQ and 3HDQ in their mode of actions. FIG. 3B illustrates potential interactions of DQ and 3HDQ with DNA and protein within fungal cells.

DETAILED DESCRIPTION

Figure 1A:
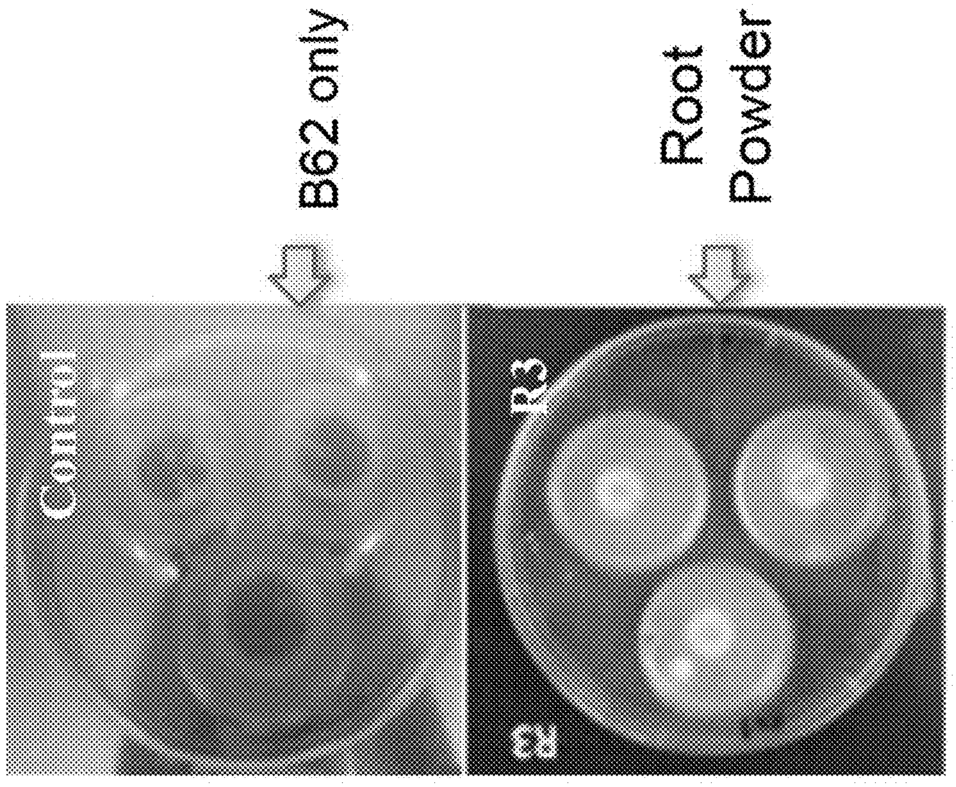
FIG. 1A-1D illustrate inhibition of fungal growth by *Diospyros mafiensis* extracts and compounds.

Compositions are described herein that include compounds that inhibit the biosynthesis of mycotoxins and fungal sporulation. The compounds are useful for inhibiting mold. For example, the compounds and compositions can be used in situations involving the growth and storage of agricultural products, where elimination of mycotoxins is desirable. Methods of using such compositions that involve applying the compositions to plants, plant parts (e.g., nuts or seeds), structures, containers, and other surfaces are also described herein.

Compounds useful for inhibiting the biosynthesis of mycotoxins and fungal sporulation can have formula I:

A-linkage-B where:

A and B are bicyclic rings with 8 to 12 ring atoms, each of the A and B bicyclic rings having (i) at least three oxygen-containing substituents selected from hydroxy (—OH), oxy (═O), ether (—O—), and alkoxy (R—OH, where R is a lower alkyl), and (ii) one or two lower alkyl substituents; and linkage is a covalent bond or a lower alkylene (e.g., $-(CH_2)_n-$, where n is an integer of 1-3) bonded to the A and B bicyclic rings.

In some cases, one of the A or B bicyclic rings has an ether where two adjacent ring atoms are bonded to an oxygen atom, thereby forming a third ring joined to the A or B bicyclic ring where the third ring has three atoms, one of which is the oxygen atom, and two of which are A or B ring atoms. Hence, in some cases compounds useful for inhibiting the biosynthesis of mycotoxins and fungal sporulation can, for example, have formula IIa or IIb:

IIa

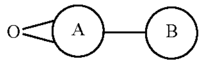

IIb

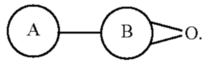

In some cases, both of the A and B bicyclic rings have 3 or 4 oxygen-containing substituents selected from hydroxy (—OH), oxy (═O), ether (—O—), and alkoxy (R—OH, where R is a lower alkyl). In some cases, one of the A or B rings has three oxygen-containing substituents, while the other of the A or B rings has four oxygen-containing substituents.

In some cases one of the A rings has two oxy substituents. In some cases one of the B rings has two oxy substituents. For example, in some cases compounds useful for inhibiting the biosynthesis of mycotoxins and fungal sporulation can, for example, have formula IIIa, IIIb, IIIc, or IIId:

IIIa

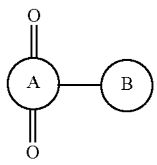

IIIb

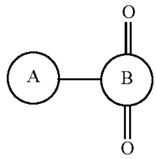

IIIc

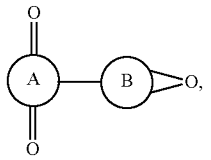

or

IIId

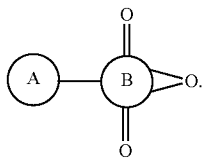

In some cases one of the A rings and one of the B rings has two oxy substituents. For example, in some cases compounds useful for inhibiting the biosynthesis of mycotoxins and fungal sporulation can, for example, have formula IVa or IVb, IVa

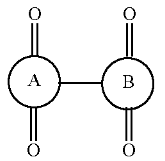

or

IVb

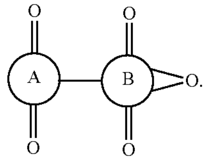

In some cases one of the A rings has one or to hydroxy substituents. In some cases one of the B rings has one or to hydroxy substituents. In some cases the A ring or the B ring has one hydroxy substituent, while the other of the A ring or the B ring has two hydroxy substituents. These hydroxy substituents can be in addition to any oxy substituents that the A or B bicyclic rings may have.

In some cases, one of the rings of the A bicyclic ring is an aromatic ring. In some cases, one of the rings of the B bicyclic ring is an aromatic ring. In some cases, one of the rings of the A bicyclic ring and one of the rings of the B bicyclic ring is an aromatic ring.

Aromatic rings are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, Aromatic rings contain about 6 to about 14 carbons in the ring portions of the groups. Aromatic rings can be unsubstituted or substituted, as defined above. Representative substituted aromatic rings can be substituted more than once, such as, but not limited to, 2-, 3-, 4-, 5-, or 6-substituted phenyl or 3-8 substituted naphthyl group s, which can be substituted with carbon or non-carbon groups such as those listed above.

In some cases, one of the rings of the A bicyclic ring has one or two double bonds (one or two unsaturations). In some cases, one of the rings of the B bicyclic ring has one or two double bonds (one or two unsaturations). In some cases, one of the rings of the A bicyclic ring and one of the rings of the B bicyclic ring has one or two double bonds (one or two unsaturations).

In some cases one of the rings of the A bicyclic ring has one or two lower alkyl substituents. In some cases one of the rings of the B bicyclic ring has one or two lower alkyl substituents. In some cases one of the rings of the A bicyclic ring has one or two lower alkyl substituents, and one of the rings of the B bicyclic ring has one or two lower alkyl substituents.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Lower alkyl groups have about 1 to about 3 carbon atoms. The term "alkylene" means a chain of methylene $(CH_2)_n$ residues, where n is 1 or 2, and where each end of the chain is linked to another moiety.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein. A lower alkoxy group has about 1 to about 3 carbon atoms.

All chiral, diastereomeric, racemic forms of a structure are intended to be embraced by the claims, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The term "salt" generally refers to forms of a compound derived from contacting the compound with an organic or inorganic acid, such as hydrochloric acid, hydrobromic acid, tartaric acid, methylsulfonic acid, acetic acid, maleic acid, and oxalic acid, to form the hydrochloride, hydrobromide, tartarate, methylsulfonate, acetate, maleate, and oxalate salt of the compound. The term "salt" also generally refers to forms of a compound derived from contacting the compound with a base to form, for example, the sodium, potassium, calcium, magnesium, ammonium, and tetraalkylammonium salt of the compound.

Some specific examples of compounds useful for inhibiting the biosynthesis of mycotoxins and fungal sporulation can have the following structures,

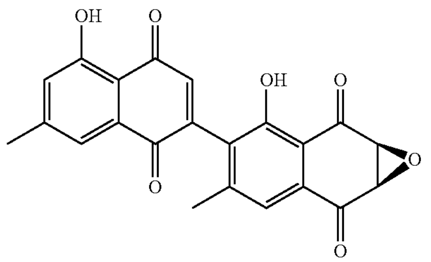

or

Diosquinone (DQ)

-continued

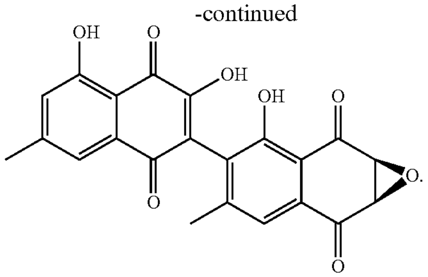

3-Hydroxydiosquinone (3HDQ)

The compounds can be isolated from *Diospyros mafiensis* F. White. *Diospyros mafiensis* F. White is a medicinal shrub or small tree (6 m tall) widely distributed in the Zanzibar-Inhambane regional mosaic and traditionally used to treat leprosy, diarrhea, and skin fungal infections in Tanzania and Mozambique. As illustrated herein, compounds present in *Diospyros mafiensis* F. White have anti-aflatoxigenic properties of compounds against vegetative growth, sporulation and aflatoxin production by fungi such as *Aspergillus flavus* and *Aspergillus parasiticus*. Bioassay-guided extraction, fractionation, and isolation of bioactive compounds using *A. parasiticus* B62 were employed.

The compounds can be isolated, for example, from root materials of *Diospyros mafiensis* F. White. In some cases, the compounds can be extracted using alcohol, for example, methanol, ethanol, or propanol. Sequential extractions at room temperature with methanol, ethyl acetate and hexane can also be performed. However, bioassays of resulting extracts showed that anti-fungal activity was improved when using a methanol extraction.

Extracts can be fractionated by any convenient process, for example, according to various chemical or physical properties of the compounds to be isolated. Fractionation methods such as by size fractionation (e.g, gel filtration, electrophoretic separation, gradient centrifugation, thin layer chromatography, or a combination thereof), ion exchange fractionation (e.g., anion exchange chromatography, cation exchange chromatography, membrane exchange chromatography, or a combination thereof), high performance liquid chromatography (HPLC), or a combination thereof.

The extraction liquid containing the compounds can be removed by evaporation at a variety of convenient temperatures (e.g., at −20° C. to 40° C.). A vacuum can be used to facilitate solvent removal. For example, solvents can be removed by freeze-drying.

The bioactive compounds can be characterized or identified using $^{1}H$ and $^{13}C$NMR and LC-M S as illustrated herein.

Growth inhibition can be assessed by measuring the colony diameter of fungal species growth. For example, growth inhibition can be assessed by measuring the colony diameter of *A. flavus* AF3357 and *A. parasiticus* SU-1 ATCC56775. Inhibitory effects on sporulation can be estimated using a hematocytometer.

Total aflatoxin present in assay mixture can be quantified by direct competitive enzyme-linked immunosorbent assay (ELISA).

Bioactive compounds Diosquinone (DQ) and 3-Hydroxydiosquinone (3HDQ) were identified and characterized. The DQ compound weakly inhibited *A. flavus* and *A. parasiticus* vegetative growth ($MIC_{50}$>100 μg/mL). The 3HDQ strongly inhibited *A. flavus* ($MIC_{50}$=14.9 μg/mL) and *A. parasiticus* ($MIC_{50}$=39.1 μg/mL). DQ strongly reduced total aflatoxin production by *A. flavus* from 157 to 36 ng/plate, and by *A. parasiticus* from 1145 ng/plate to 45 ng/plate at 100 μg/mL. 3HDQ reduced total aflatoxin production by *A. parasiticus* from 1145 to 32 ng/plate; stimulated production by *A. flavus* from 157 to 872 ng/plate at 12.5 μg/mL but reduced to 45 ng/plate at 100 μg/mL. In summary, DQ and 3HDQ are antifungal compounds that prevent mold growth and aflatoxin accumulation in food and feed.

Compositions

Compositions described herein can include at least one compound of formula I, formula IIa, formula IIb, formula IIIa, formula IIIb, formula IIIc, formula IIId, formula IVa, and/or formula IVb. Compositions described herein can include at least one of diosquinone or 3-hydroxy diosquinone (3HDQ). Compositions described herein can include a combination of diosquinone and 3-hydroxy diosquinone (3HDQ). The compositions can also include additional components such as a carrier, solvent, surfactant, an additional active ingredient, or a combination thereof.

These compositions are useful as antibiotics and antifungal composition

The composition can contain varying amounts of the compounds described herein. For example, the compounds can be present in liquid compositions at a concentrations of about 0.1 μg/mL to about 1000 μg/mL, or about 1 μg/mL to about 800 μg/mL, or about 3 μg/mL to about 600 μg/mL, or about 5 μg/mL to about 500 μg/mL, or about 5 μg/mL to about 300 μg/mL.

In dry compositions, the compounds can be present in at weight/weight concentrations of about 0.1 μg/g to about 1000 μg/g or about 1 μg/g to about 800 μg/g, or about 3 μg/g to about 600 μg/g or about 5 μg/g to about 500 μg/g or about 5 μg/g to about 300 μg/g.

The compositions can therefore be dry compositions or liquid compositions.

In some instances, the compounds are dissolved in a solvent to form a liquid composition with a known concentration of at least one compound described herein. The solvent can be an alcohol. For example, the solvent can be ethanol, methanol, isopropyl alcohol, or a combination thereof.

The compositions can contain a carrier such as an emulsifier, a dispersing agent, thickening agent, a surfactant, a clay, a polymer, a colorant, a wetting agent of ionic or non-ionic type, a natural or regenerated mineral substance, a dispersant, a wetting agent, a tackifier, a thickener, a binder, or a mixture of such carriers. For example, the compositions can contain polyacrylic acid salts, lignosulphonic acid salts, phenolsulphonic or naphthalenesulphonic acid salts, poly condensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxy ethylated alcohols or phenols, fatty acid esters of polyols, and derivatives of the present compounds containing sulfate, sulfonate and phosphate functions. The presence of at least one surfactant can be included when the active compound and/or the inert support are water-insoluble and when the vector agent for the application is water. For example, surfactant content can be about 5% to 40% by weight of the composition.

Coloring agents such as inorganic pigments can be present in the composition, for example iron oxide, titanium oxide, ferrocyan blue, and organic pigments such as alizarin, azo and metallophthalocyanine dyes, and trace elements such as iron, manganese, boron, copper, cobalt, molybdenum and zinc salts can be used. The compounds can be present in paints along with any available coloring material (s) and other components typically employed in paints.

Optionally, other additional components may also be included, e.g. protective colloids, adhesives, thickeners, thixotropic agents, penetration agents, stabilizers, sequestering agents.

The compositions can also include other ingredients. For example, bactericidal compounds can be employed. Such compounds are useful in crop protection for example for controlling Pseudomonadaceae, Rhizobiaceae, Enterobacteriaceae, Corynebacteriaceae and Streptomycetaceae. In addition, the compounds described herein can be used together in a composition or they can be used concomitantly with one or more of the other agrichemicals such as various pesticides, acaricides, nematicides, other types of fungicides, and plant growth regulators.

Various types of fungicides can optionally be included in the compositions described herein. Examples include copper fungicide such as basic copper chloride and basic copper sulfate, sulfur fungicide such as thiuram, zineb, maneb, mancozeb, ziram, propineb, and polycarbamate, polyhaloalkylthio fungicide such as captan, folpet, dichlorfluanid, organochlorine fungicide such as chlorothalonil, fthalide, organophosphorous fungicide such as O,O-bis(1-methylethyl) S-phenylmethyl phosphorothioate (IBP), edifenphos (EDDP), tolclophos-methyl, pyrazophos, fosetyl, dicarboxylmide fungicide such as iprodione, procymidone, vinclozolin, fluoromide, carboxyamide fungicide such as oxycarboxin, mepronil, flutolanil, tecloftalam, trichlamide, pencycuron, acylalanine fungicide such as metalaxyl, oxadixyl, furalaxyl, methoxyacrylate fungicides such as kresoxim-methyl (stroby), azoxystrobin, metominostrobin, trifloxystrobin, pyraclostrobin, anilinopyrimidine fungicide such as andupurine, mepanipyrim, pyrimethanil, cyprodinil, antibiotic agents such as polyoxin, blasticidin S, kasugamycin, validamycine, dihydrostreptomycin sulfate, propamocarb hydrochloride, quintozene, hydroxy isoxazole, methasulfocarb, anilazine, isoprothiolane, probenazole, chinomethionat, dithianon, dinocap, diclomezine, ferimzone, fluazinam, pyroquilon, tricyclazole, oxolinic acid, iminoctadine acetate, iminoctadine albesilate, cymoxanil, pyrrolnitrin, diethofencarb, binapacryl, lecithin, sodium bicarbonate, fenaminosulf, dodine, dimethomorph, phenazine oxide, carpropamide, flusulfamide, fludioxonil, famoxadone, or combinations thereof. Hence, other types of fungicides can be mixed together with and used in various amounts with one or more of the compounds described herein.

The compounds described herein can be used in a weight ratio relative to the other type of fungicide such as from 1:0.001 to 1:1000 as a weight ratio. In some instance, a compound of formula IA, IB, or II relative to the other type of fungicide can vary from 1:0.01 to 1:100 as a weight ratio.

Pesticides can be included in the compositions, with any of the compounds described herein. The pesticides can include organophosphorous pesticides, carbamate pesticides such as fenthion, fenitrothion, diazinon, chlorpyrifos, ESP, vamidothion, phenthoate, dimethoate, formothion, malathon, trichlorfon, thiometon, phosmet, dichlorvos, acephate, EPBP, methylparathion, oxydemeton-methyl, ethion, salithion, cyanophos, isoxathion, pyridaphenthion, phosalone, methidathion, sulprofos, chlorfevinphos, tetrachlorvinphos, dimethylvinphos, propaphos, isofenphos, ethylthiometon, profenofos, pyraclofos, monocrotophos, azinphosmethyl, aldicarb, methomyl, thiodicarb, carbofuran, carbosulfan, benfuracarb, furathiocarb, propoxur, BPMC, MTMC, MIPC, carbaryl, pirimicarb, ethiofencarb, and fenoxycarb, pyrethroid pesticides such as permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, ethofenprox, cycloprothrin, tralomethrin, silafluofen, brofenprox, and acrinathrin, and benzoylurea and other types of pesticides such as diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotin sulfate, rotenone, mataldehyde, machine oil, and microbial pesticides e.g. BT and insect pathogenic virus.

Acricides can be included in the compositions described herein. The acricides that can be employed include, for example, chlorbenzilate, phenisobromolate, dicofol, amitraz, BPPS, benzomate, hexythiazox, fenbutatin oxide, polynactin, chinomethionat, CPCBS, tetradifon, avermectin, milbemectin, clofentezin, cyhexatin, pyridaben, fenpyroximate, tebufenpyrad, pylidimifen, fenothiocarb, and dienochlor.

As for the aforementioned nematicides, fenamiphos, fosthiazate and the like can be specifically exemplified; as for plant-growth regulators, gibberellins (e.g., gibberellin A3, gibberellin A4, and gibberellin A7), auxin, 1-naphthaleneacetic acid, and so on can be specifically exemplified.

More generally, the active compounds can be combined with any solid or liquid additive, which complies with the usual formulation techniques. In general, the composition according to the invention may contain from 0.05 to 99% by weight of active compounds, preferably from 10 to 70% by weight.

The compounds or compositions can be provided in a form that is ready-to-use or in a form that can be prepared for use. The compounds or compositions can be applied by a suitable device, such by use of a spraying or dusting device. The compounds or compositions can be applied by use of brush or roller.

The compounds or compositions can be provided in concentrated commercial compositions that should be diluted before application to the crop. For example, the compounds can provided in dry (e.g., lyophilized) form, or in concentrated form, and then dissolved or diluted as desired. The compositions can be in formulated into an aerosol dispenser, as a capsule suspension, as a cold fogging concentrate, as a dustable powder, as an emulsifiable concentrate, as an emulsion oil in water, as an emulsion water in oil, as an encapsulated granule, as a fine granule, as a flowable concentrate for seed or nut treatment, as a gas (under pressure), as a gas generating product, as granules, as a hot fogging concentrate, as macrogranules, as microgranules, as an oil dispersible powder, as an oil miscible flowable concentrate, as an oil miscible liquid, as a paste, as a plant rodlet, as a powder for dry seed or nut treatment, as seeds or nuts coated with the composition, as a soluble concentrate, as a soluble powder, as a solution for seed (or other) treatment, as a suspension concentrate (flowable concentrate), as an ultra-low volume (ULV) liquid, as an ultra-low volume (ULV) suspension, as water dispersible granules or tablets, as a water dispersible powder for slurry treatment, as water soluble granules or tablets, as a water soluble powder for seed or nut treatment, as a wettable powder, or as a combination thereof (e.g., two types of formulations packaged together).

Mycotoxins

The compounds, compositions, and methods described herein can inhibit biosynthesis of a variety of mycotoxins. For example, *Aspergillus flavus* and *Aspergillus parasiticus* produce toxic secondary metabolites called aflatoxins, which have deleterious health effects to humans and animals. Such deleterious health effects can include immunosuppression (Jiang et al., 2008), growth impairment (Khlangwiset et al., 2011), aflatoxicosis (Strosnider et al., 2006) and liver cancer (Liu and Wu, 2010).

The World Health Organization (2008) estimated that between 25,000 and 155,000 people die each year of liver cancer linked to chronic exposure to aflatoxins through contaminated food, and over 83% of such deaths occur in Sub-Saharan African countries (Liu and Wu, 2010; Strosnider et al., 2006). Unfortunately, severe fungal deterioration and contamination of food occur during storage due to conditions favorable to fungal growth (Hell et al., 2000). Additionally, chronic exposure to *A. flavus* and *A. parasiticus* spores is now known to cause a respiratory disease called allergic bronchopulmonary aspergillosis (ABPA). Although ABPA occurs relatively infrequently, it can be deadly particularly for immunocompromised individuals (Denning et al., 2013). Denning and coworkers (2013) calculated an estimate of 389,900 cases of ABPA associated with invasive fungal infections is likely in Africa. Thus, individuals winnowing infected seeds during harvesting or from granaries without dust masks are likely to inhale fungal spores and thus, may be at risk of ABPA and invasive aspergillosis (Pfaller et al., 2016), which are often accompanied with chronic asthma (Denning et al., 2013).

In recent years, there have been growing concerns associated with the indiscriminate use of synthetic pesticides for crop protection against the molds in storage. The concerns associated with synthetic pesticides include fungal resistance, toxicological effects on consumers, non-biodegradability, and prohibitive costs (da Cruz Cabral et al., 2013). As an alternative to synthetic pesticides, medicinal plants may be useful sources of naturally-occurring biodegradable, readily available, and inexpensive food preservatives that could be useful to prevent growth, sporulation and aflatoxin production by aflatoxigenic molds in food during storage (Bluma et al., 2008; Bluma and Etcheverry 2008; Velazhahan et al., 2010; El-Nagerabi et al., 2013; Alejandra et al., 2013; Kedia et al., 2014; and Prakash et al., 2014). These studies showed that exposure of *A. flavus* and *A. parasiticus* to medicinal plant extracts or pure compounds significantly reduced or completely inhibited their growth and toxin production. Additionally, because such extracts contain a variety of compounds, their synergistic modes of action against molds may reduce the likelihood of development of resistance unlike that related to use of individual synthetic pesticides (da Cruz Cabral et al., 2013).

Mycotoxins are toxic fungal metabolites, often found in agricultural products that are characterized by their ability to cause health problems for humans and vertebrates. Mycotoxins include compounds such as aflatoxins, ochratoxins, patulin, fumonisins, zearalenones, and trichothecenes. They are produced for example by different *Fusarium, Aspergillus, Penicillium* and *Alternaria* species.

Aflatoxins are toxins produced by *Aspergillus* species that grow on several crop s, in particular on maize or corn before and after harvest of the crop as well as during storage. The biosynthesis of aflatoxins involves a complex polyketide pathway starting with acetate and malonate. One important intermediate is sterigmatocystin and O-methylsterigmatocystin which are direct precursors of aflatoxins. Important producers of aflatoxins are *Aspergillus flavus*, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* sp p., *Chaetomium* sp p., *Farrowia* sp p., and *Monocillium* sp p., in particular *Aspergillus flavus* and *Aspergillus parasiticus* (Plant Breeding (1999), 118, pp 1-16). There are also additional *Aspergillus* species known. The group of aflatoxins consists of more than 20 different toxins, for example, aflatoxin B1, B2, G1 and G2, cyclopiazonic acid (CPA).

Ochratoxins are mycotoxins produced by some *Aspergillus* species and *Penicilium* species, like *A. ochraceus, A. carbonarius* or *P. viridicatum*, Examples for Ochratoxins are ochratoxin A, B, and C. Ochratoxin A is the most prevalent and relevant fungal toxin of this group.

Fumonisins are toxins produced by *Fusarium* species that grow on several crop s, mainly corn, before and after harvest of the crop as well as during storage. The diseases, *Fusarium* kernel, ear and stalk rot of corn, is caused by *Fusarium verticillioides, Fusarium subglutinans, Fusarium moniliforme*, and *Fusarium proliferatum*. The main mycotoxins of these species are the fumonisins, of which more than ten chemical forms have been isolated. Examples for fumonisins are FB I, FB2 and FB3. In addition the above mentioned *Fusarium* species of corn can also produce the mycotoxins moniliformin and beauvericin. In particular *Fusarium verticillioides* is mentioned as an important pathogen of corn, this *Fusarium* species produces as the main mycotoxin fumonisins of the B-type. Trichothecenes are those mycotoxins of primary concern which can be found in *Fusarium* diseases of small grain cereals like wheat, barley, rye, triticale, rice, sorghum and oat. They are sesquiterpene epoxide mycotoxins produced by species of *Fusarium, Trichothecium*, and *Myrothecium* and act as potent inhibitors of eukaryotic protein synthesis. Some of these trichothecene producing *Fusarium* species also infect corn or maize.

Examples of trichothecene mycotoxins include T-2 toxin, HT-2 toxin, isotrichodermol, diacetoxyscirpenol (DAS), 3-deacetylcalonectrin, 3, 15-dideacetylcalonectrin, scirpentriol, neosolaniol; 15-acetyldeoxynivalenol, 3-acetyldeoxynivalenol, nivalenol, 4-acetylnivalenol (fusarenone-X), 4, 15-diacetylnivalenol, 4,7,15-acetylnivalenol, and deoxynivalenol ("DON") and their various acetylated derivatives. The most common trichothecene in *Fusarium* head blight is deoxynivalenol produced for example by *Fusarium gramninearum* and *Fusarium culmorum.*

Another my cotoxin mainly produced by *F. culmorum, F. graminearum* and *F. cerealis* is zearalenone, a phenolic resorcyclic acid lactone that is primarily an estrogenic fungal metabolite.

*Fusarium* species that produce mycotoxins, such as fumonisins and trichothecenes, include *F. acuminatum, F. crookwellense, F., verticillioides, F. culmorum, F. avenaceum, F. equiseti, F. moniliforme, F, graminearum* (*Gibberella zeae*), *F. lateritium, F. poae, F. sambucinum* (*G. pulicaris*), *F. proliferatum, F. subglutinans, F. sporotrichioides* and other *Fusarium* species.

In contrast the species *Microdochium nivale* also a member of the so-called *Fusarium* complex is known to not produce any mycotoxins. Both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy grain toxicoses in animals, including anemia and immunosuppression, hemorrhage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of over-wintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, DON. Trichothecenes were detected in the toxic grain samples responsible for recent human disease outbreaks in India and Japan. There exists, therefore, a need for agricultural methods for preventing and crops having reduced levels of, mycotoxin contamination. Further, mycotoxin-producing *Fusarium* species are destructive pathogens and attack a wide range of plant species. The acute phytotoxicity of mycotoxins and their occurrence in plant tissues also suggests that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

*Stachybotrys* spp., known as the toxic black molds in buildings, produce trichothecene and atranone mycotoxins that affect human health. These products could be used in paints or plasterboard to inhibit the growth and sporulaiton of *Stachybotrys* in damp building environments.

The compounds described herein can be used to inhibit biosynthesis of any such mycotoxins.

Treatment

The compounds and compositions described herein can be used as antibiotic formulations for treatment of animals, including humans, domesticated animals, zoo animals, and wild animals. Plants, seeds, and plant products can also be treated with the compounds and/or compositions described herein. A method can be employed that includes administering any of the compounds or compositions described herein to one or more animals, one or more plants, one or more plant seeds, or one or more plant products.

The compounds described herein can also be applied to structures (e.g, houses, barns, sheds, warehouses, basements, attics, closets, bathrooms, cupboards, storage bins, storage containers, etc.) where mold or fungi is present or may grow. For example, the compounds described herein can be applied to moist areas and/or areas suspected of developing fungal growth. Examples of areas where the compounds and/or compositions can be applied include laundry rooms, bathrooms, bedrooms, closets, basements, attics, kitchens, cabinets, animal pens, storage areas, silos, grain bins, siding decks, boat surfaces, and the like.

Application of compounds or compositions can be carried out directly, or by action on their environment, habitat or storage area. Application (or treatment) methods include, for example, topical application, oral administration, or parenteral administration to an animal. Application (or treatment) methods can also include, for example, watering (drenching), drip irrigation, spraying atomizing broadcasting dusting foaming spreading-on, brushing on, and combinations thereof. Plants, seeds, plant products, surfaces, and/or structure can be treated by powdering spraying mixing encrusting or a combination thereof. The compositions can be applied in dry or liquid form.

The compounds and compositions described herein can be employed for reducing mycotoxin contamination or in the protection of animals, materials, surfaces, products, and combinations thereof. The compounds or compositions according to the invention can be used to curatively or preventively reduce the mycotoxin synthesis by fungi. For example, a method can be employed for curatively or preventively reducing mycotoxin contamination by application or administration of a compound, or a composition comprising a compound, according to any of the formulae described herein to an animal, a plant seed, a plant, a plant product, or to the fruit of the plant or to the soil in which the plant is growing or in which it is desired to grow.

When applying the compounds or compositions described herein, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of seeds, plant cutting or twigs serving propagation. The compounds and/or compositions are also useful in reducing mycotoxin contamination when they are applied to a plant, plant see, plant product, and/or plant propagation material in an effective amount before and/or after harvest and/or during storage.

An effective amount is an amount sufficient to reduce fungal growth or mycotoxin production by at least about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%. For example, in some cases the compounds described herein can each be administered or applied at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.

In some instances, the compounds and/or compositions are provided as concentrated formulation that are diluted ten-fold, 100-fold, or 1000-fold to provide a concentration that is applied or administered to animals, structures, walls, floors, ceilings, containers, plants, seeds, and/or plant products.

The period of time within which protection is effective generally extends from 1 to 90 day s, from 1 to 80 day s, from 1 to 70 day s, from 1 to 60 day s, from 1 to 45 day s, from 1 to 30 days, from 1 to 14 days, or from 1 to 7 days, after application of the compounds and/or compositions described herein.

At certain application rates, the active compound combinations can, for example, have a strengthening effect in plants. For example, the compounds and/or compositions can also mobilize the defense system of the plant against attack by unwanted phytopathogenic fungi and/or microorganisms and/or viruses. This may, if appropriate, be one of the reasons of the enhanced activity of the combinations according to the invention against biosynthesis of mycotoxins.

The compositions described herein can include at least one compound described herein and at least one carrier. The compositions described herein can be used to reduce fungal infection and/or release of toxins associated with fungi. The compositions can optionally include one or more antibacterial or other antifungal agents.

Compositions described herein can be administered so as to ameliorate one or more symptoms of disease. In some embodiments, the compositions can be administered so as to achieve a reduction in at least one symptom associated with fungal infections. Such symptoms can include itching swelling irritation, exhaustion, chronic sinus problems, allergies, joint pain, digestive problems (gas and bloating), urinary tract infections, or combinations thereof.

Fungal infections of the skin can be common and include athlete's foot, jock itch, ringworm, yeast infections, vaginal fungal infections, urinary tract infections, oral thrush, vaginal yeast infection, nail fungus, diaper rash.

The compositions are particularly amenable to formulation into pharmaceutical compositions.

To achieve the desired effect(s), the compounds, or combination thereof may be administered in single or divided dosages. For example, the compounds can be present in the compositions in amounts of at least about 0.01 mg/kg to about 100 mg/kg of at least about 0.01 mg/kg to about 300 to 500 mg/kg at least about 0.1 mg/kg to about 100 to 300 mg/kg or at least about 1 mg/kg to about 50 to 100 mg/kg of body weight, although other dosages may provide beneficial results.

The amount administered will vary depending on various factors including but not limited to, what types of compound(s), and/or other therapeutic agents are administered, the route of administration, the progression or lack of progression of the disease, the weight, the physical condition, the health, the age of the patient, whether prevention or treatment is to be achieved, and if the antigen or ligand is chemically modified. Such factors can be readily determined by the clinician employing animal models or other test systems that are available in the art.

Compounds and compositions thereof may be administered in a single dose, in multiple doses, in a continuous or intermittent manner, depending for example, upon the recipient's physiological condition, whether the purpose of the administration is therapeutic or prophylactic, and other factors known to skilled practitioners. The administration of the compositions may be essentially continuous over a pre-selected period of time or may be in a series of spaced doses. Both local and systemic administration is contemplated.

To p rep are the composition, the compounds are synthesized or otherwise obtained, and purified as necessary or desired. These compounds can then be lyophilized or stabilized, for example, if storage is desirable. The compounds can be combined with a carrier such as a solvent, liposome or particle. The concentrations of the agents can be evaluated and adjusted to an appropriate amount, and these therapeutic agents can optionally be combined with other agents.

In general, dosage forms of the invention comprise an amount of at least one of compounds effective to treat or prevent the clinical symptoms of an infection. Any statistically significant attenuation of one or more symptoms of an infection is considered to be a treatment thereof. The absolute weight of a given compound that is included in a unit dose can vary widely. For example, about 0.01 to about 2 g or about 0.1 to about 500 mg of at least one compound can be administered. Alternatively, the unit dosage can vary from about 0.01 g to about 50 g from about 0.01 g to about 35 g from about 0.1 g to about 25 g from about 0.5 g to about 12 g from about 0.5 g to about 8 g from about 0.5 g to about 4 g or from about 0.5 g to about 2 g.

Daily doses of one or more compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

The compositions can include a carrier such as a pharmaceutically acceptable carrier. By "pharmaceutically acceptable" it is meant a pharmaceutical carrier, diluent, excipient, and/or salt that is compatible with the other ingredients of the formulation, and not deleterious to the recipient thereof. Note that the carriers associated with one or more compounds, or combinations thereof can be distinct from the "pharmaceutically acceptable carrier" or a "pharmaceutical carrier" described in this section. Thus, a "pharmaceutically acceptable carrier" or a "pharmaceutical carrier" is a non-active ingredient that is not deleterious to the recipient thereof and that can solubilize or disperse the active ingredients to facilitate formulation of a convenient dosage form.

One or more suitable unit dosage forms comprising the compounds of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The compounds may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid solutions, solid matrices, semi-solid pharmaceutical carriers, finely divided solid pharmaceutical carriers or combinations thereof, and then, if necessary, introducing or shaping the product into the desired delivery system.

Pharmaceutical formulations containing the therapeutic agents described herein can be prepared by procedures known in the art using available ingredients. The formulations can contain pharmaceutically acceptable carriers, vehicles and adjuvants. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethyleneglycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

It is possible, for example, to prep are solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," poly glycols and polyethylene glycols, $C_1$-$C_4$ alkyl esters of short-chain acids, ethyl or isopropyl lactate, fatty acid triglycerides such as the products marketed under the name "Miglyol," isopropylmyristate, animal, mineral and vegetable oils and poly siloxanes.

The compounds may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active agents and other ingredients may form suspensions, solutions, or emulsions in oily or aqueous vehicles, and may contain formulatory agents such as suspending stabilizing and/or dispersing agents.

Alternatively, the compounds and other ingredients may be in powder form, obtained by aseptic isolation of sterile solid or by lyophilization from solution, for constitution with a suitable vehicle, e.g., sterile, pyrogen-free water, before use.

When the compounds of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste.

In some case, the compositions can be prepared for, and administered as, oral compositions. For example, tablets or caplets containing the compounds, and optionally a carrier can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the compounds of the invention are designed to resist disintegration in the stomach and dissolve in the more neutral to alkaline environment of the duodenum.

Orally administered compounds can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

The compositions can also include antioxidants, surfactants, preservatives, film-forming keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the therapeutic agents are well suited to formulation as sustained release dosage forms and the like. The formulations can be so constituted that they release the active agent, for example, in a particular part of the digestive tract, vascular system or respiratory tract, possibly over a period of time. Coatings, envelopes, and protective matrices may be made, for example, from polymeric substances, such as poly lactide-glycolates, liposomes, microemulsions, microparticles, nanoparticles, or waxes. These coatings, envelopes, and protective matrices are useful to coat indwelling devices, e.g., stents, catheters, peritoneal dialysis tubing draining devices and the like.

For topical administration, the compounds may be formulated by available methods for direct application to a target area. Compositions chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soap s, detergents, lotions or cakes of soap. Other conventional forms for this purpose include wound dressings, coated bandages or other polymer coverings, ointments, creams, lotions, pastes, jellies, sprays, and aerosols.

The compositions can be delivered via patches or bandages for dermal administration. Alternatively, the therapeutic agents can be formulated to be p art of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drop s, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The compounds may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid pharmaceutical carrier.

The compositions may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

For administration by inhalation or insufflation, the composition may be in the form of a dry powder, for example, a powder mix of the therapeutic agent and a suitable powder base such as lactose or starch. The powder composition may be presented in unit dosage form in, for example, capsules or cartridges, or, e.g, gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

The compounds can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder.

It will be appreciated that the unit content of active ingredient or ingredients contained in an individual aerosol dose of each dosage form need not in itself constitute an effective amount for treating the particular immune response, allergy, asthma, anaphylaxis or other disease or condition since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the compounds are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drop s, a liquid spray, such as via a plastic bottle atomizer or metered-dose inhaler. Typical of atomizers are the Mistometer (Wintrop) and the Medihaler (Riker).

Furthermore, the compounds may also be used in combination with other therapeutic agents, for example, pain relievers, anti-inflammatory agents, antibacterial agents, anti-fungal agents, anti-cancer agents and the like, whether for the conditions described or some other condition.

Kits

The present invention further pertains to a packaged composition such as a kit or other container for detecting controlling preventing or treating an infection or fungal synthesis of a mycotoxin. The kits of the invention can be designed for detecting controlling preventing or treating problems such as those described herein (e.g., fungal growth, fungal infections, or mycotoxin production by fungi).

In one embodiment, the kit or container holds a compound as well as instructions for preparing a composition that includes the compound. The kit can also include a carrier.

In another embodiment, the kit or container holds an effective amount of a composition for treating preventing or controlling fungal growth, fungal infection, or my cotoxin production by fungi, and instructions for using the composition for control of the fungal growth, fungal infection, or my cotoxin production by fungi. The composition includes at least one compound in an amount effective for control, prevention, or treatment of fungal growth, fungal infections, or mycotoxin production by fungi. The compound(s) can be provided in combination with a carrier. Such a composition can be in liquid form, powder form or other form permitting ready application or administration.

The kits of the invention can also comprise containers with tools useful for applying the compositions, or administering the compositions of the invention. Such tools can include spreaders, brushes, mixing tools, spray devices, or a combination thereof. In some cases, such tools can include syringes, swabs, catheters, antiseptic solutions and the like.

The following non-limiting Examples illustrate some aspects of the compounds, compositions, and methods provided herein.

EXAMPLE 1

Materials and Methods

This Example describes some of the materials and methods employed in the development of the invention.

General Experimental Procedures: All solvents used for isolation and purification were of ACS reagent grade (Sigma-Aldrich Chemical Co., St. Louis, Mo., USA). Merck silica gel (60 mesh size, 35-70 μm) with a particle size of 60 μm was used for preparative medium-pressure liquid chromatography (MPLC). Silica gel plates (250 μm; Analtech, Inc., Newark, Del., USA) were used for preparative thin-layer chromatography (TLC) and developed plates viewed using ultraviolet light at 254 or 366 nm using a Spectroline CX-20 ultraviolet fluorescence analysis cabinet (Spectroline Corp., Westbury, N.Y., USA). After viewing and locating spots under UV light, plates were sprayed with 10% sulfuric acid solution in water and charred to observe spots that were not visible under UV. NMR spectra were recorded on a 500 MHz (Varian Unity±500, 1H NMR) or 125 MHz (Varian Unity±500, 13C NMR) VRX instruments. ESIMS spectra were recorded on a Waters Xevo G2-S Q-TOF LC mass spectrometer (Waters Corporation, Milford, Mass., USA). See FIGS. 1E-1H.

Plant material: Root bark of *Diospyros mafiensis* F. White was collected on Dec. 23, 2014, at the location S06° 53'33" E39° 06'01", 182 m in Kisarawe, Pugu, Dar es Salaam, Tanzania. A voucher specimen has been deposited in the Botany Department Herbarium, University of Dar es Salaam, Tanzania, for future reference (Voucher No. FMM 3693). The root bark was air-dried in the shade for five days. The dry root bark was milled using a laboratory mill (Model 4, Martha R. Thomas Company, Philadelphia, Pa., USA). The milled plant material was shipped to Michigan State University for further analyses.

Fungal strains, growth medium and growth conditions: Wild-type strains of aflatoxigenic molds *A. flavus* (AF3357), and *A. parasiticus* (SU-1, ATCC56775) and a mutant strain of *A. parasiticus* B62 were used throughout this study. The mutant *A. parasiticus* B62 strain was used for screening the anti-aflatoxigenic activities and aflatoxin reduction efficacies of the methanolic extract and fractions of the plant material. All strains were grown on glucose minimal salts (GM S), which is a chemically defined medium that was prepared as previously described (Tice and Buchanan, 1981). The pH of the medium was adjusted to 4.5 using 1M NaOH. Molds were center-inoculated onto Petri dishes and allowed to grow in the dark in an incubator at 30° C. for 5 days for screening and 10 days for bioassays of isolated bioactives against wild-type strains *A. flavus* AF3357 and *A. parasiticus* SU-1, ATCC56775.

Screening *Diospyros mafiensis* Root Powders and Methanolic Extracts Using *A. Parasiticus* Strain B62: *A. parasiticus* strain B62 accumulates the brightly colored red pigment (Lee et al., 1971), norsolorinic acid (NA), in the colony and surrounding growth medium (Roze et al., 2011). The disappearance of red coloration following treatment in the growth medium provides visual evidence of aflatoxin biosynthesis inhibition (FIG. 1). Dry root powders (10 g) were placed in a cell culture dish (150×25 mm) and evenly sp read at the bottom of the plate. Three small Petri dish (60×15 mm) covers were filled with Potato Dextrose Agar (PDA) (10 mL) growth medium. Conidiospores ($1\times10^4$ CFU/plate) of *A. parasiticus* were center-inoculated onto PDA agar medium solidified in each of small Petri dish covers. The three inoculated Petri dish covers were placed inside a larger dish that contained root powders evenly distributed at the bottom of the dish. Then, the lid of the larger dish was covered and sealed with parafilm to prevent the escape of root volatiles and the smaller dishes inside the larger dish were open to allow free interactions of gases emanating from the root powders to the growing fungus. The control set was prepared the same way, but the larger dish contained no root powders (Roze et al., 2007; Roze et al., 2011). The fungus was allowed to grow in the dark at 30° C. for three days.

An appropriate mass of powdered root methanolic extract (25, 50, and 250 mg) (extraction method is described in next section) was dissolved in 1 mL of dimethylsulfoxide (DMSO) to make stock solutions containing 25, 50 and 250 mg/mL, respectively. Flat-bottomed 6-well culture plates (SIAL0516, Sigma-Aldrich, St Louis, Mo. 63103, USA) were used to grow the molds in triplicate. From each stock concentration, 10 µL were placed into each of the three plates per treatment. Then molten GM Sagar tempered to 50° C. (5 mL) was poured into each plate while shaking to ensure homogeneous mixing of the contents. Plates were allowed to cool and solidify the agar. The concentrations in the growth medium were 50, 100, and 500 µg/mL, from the stock solutions 25, 50, 250 mg/mL, respectively. Controls included (1) GMS without extract and (2) GMS without extract but with 10 µL DMSO. Then, conidiospores ($1\times10^4$ CFU/plate) of *A. parasiticus* B62 were center-inoculated onto the GMS agar medium of each plate and incubated in the dark at 30° C. for 5 days.

Bioassay-Guided Extraction and Isolation: The plant material (e.g., *Diospyros* mafiensis) was initially extracted sequentially at room temperature with methanol, ethyl acetate and hexane. Bioassays of resulting extracts showed activity limited to methanolic extract. Subsequently, powdered root barks (200 g) were extracted with methanol (1.5 L, 24 h×3), and evaporation of the solvent under vacuum afforded a powdered extract (57.30 g). An aliquot (20 g) was stirred in methanol (200 mL, 1 h) and centrifuged at room temperature for 10 min to afford residue A (0.75 g, plant material) and supernatant. The supernatant was evaporated under vacuum to obtain methanol-free reddish residue B (19.13 g). This residue (19.13 g) was then mixed with hexane (200 mL) and stirred for 1 h and centrifuged at room temperature for 10 min to afford precipitate C (16.66 g) and supernatant, which was evaporated under vacuum to obtain oily fraction D (2 g). The precipitate C was mixed with 200 mL of ethylacetate, stirred for 1 h, and centrifuged at room temperature for 10 min to afford a precipitate F (12.22 g) and supernatant E. Evaporation of ethylacetate from the supernatant under vacuum afforded fraction E (4.15 g). An aliquot of fraction E (350 mg) was mixed with acetone (6 mL) and stirred for 1 h and centrifuged at room temperature for 10 min to obtain precipitate E1 (17.5 mg) and supernatant. The precipitate E1 (17.5 mg) was soluble in methanol. To the acetone supernatant, hexane (7 mL) was added and the mixture was stirred for 1 h and centrifuged at room temperature for 10 min to obtain subfraction (residue) E2 (133 mg). The supernatant, acetone-hexane mixture, was evaporated to obtain subfraction E3 (198 mg) (Alexander-Lindo et al., 2004).

Fractions A, B, D, E, and F, and sub-fractions E1, E2, and E3 were distinct, as detected by TLC analyses and screening against *A. parasiticus* B62 grown in the dark at 30° C. for 5 days. Sub-fraction E1 was inactive. All fractions (A-F) and sub-fraction E2 were weakly active as indicated by FIG. 1C. Sub-fraction E3 exhibited the strongest activity and was preferentially selected for isolation, purification and characterization of bioactive compounds. An aliquot of E3 (120 mg) was purified by preparative TLC ($CHCl_3$: MeOH 30:1 v/v, two runs) to yield compounds 1 (23 mg) and 2 (9.2 mg).

Characterization of Compounds 1 and 2:

Compound 1: Red solid; $^1H$ NMR (500 MHz, $CDCl_3$): 11.85 (1H, s, 5-OH), 11.48 (1H, J=10.8 Hz, 5'-OH), 7.48 (2H, d, 5.4 Hz, H-8, H-8'), 7.11 (1H, s, H-6), 6.85 (1H, d, 12.7 Hz, H-3), 4.01 (1H, s, H-3'), 3.96 (1H, s, H-2'), 2.44 (3H, s, H-7$CH_3$), 2.27 (3H, s, H-7'$CH_3$); $^{13}C$ NMR (125 MHz, $CDCl_3$): 195.3, 195.1 (C-4'), 189.6, 189.4 (C-1'), 188.8 (C-4), 182.4 (C-1), 161.4 (C-5), 159.2 (C-5'), 148.7 (C-7), 147.5 (C-7'), 145.5, 145.4 (C-2), 138.9, 138.7 (C-3), 129.1 (C-9, C-9'), 124.2 (C-6'), 121.3 (C-6), 121.1 (C-8, C-8'), 113.1 (C-10'), 112.1 (C-10), 55.4 (C-2'), 55.1 (C-3'), 22.3 (C-11), 22.1 (C-11'). See FIG. 1E.

These data revealed that compound 1 was diosquinone (DQ). Based on spectral data, DQ was previously reported from the roots of the same plant (Khan and Rwekika, 1999).

Compound 2: Red solid; $^1$H NMR (500 MHz, $CD_3OD$): 7.45 (1H, s, H-8'), 7.36 (1H, s, H-8), 6.92 (1H, H-6), 3.99 (2H, dd, H-2', H-3'), 2.40 (3H, s, H-7$CH_3$), 2.26 (3H, s, H-7'$CH_3$); $^{13}$C NMR (125 MHz, $CD_3OD$): 197.4, (C-4'), 191.7 (C-1'), 190.4 (C-4), 182.1 (C-1), 170.1 (C-3), 163.1 (C-5), 161.8 (C-5'), 150.9 (C-7), 150.1 (C-7'), 136.6 (C-2), 133.6 (C-9, C-6'), 131.3 (C-9'), 121.7 (C-6), 121.5 (C-8'), 120.4 (C-8), 113.2 (C-10'), 113.1 (C-10), 56.8 (C-2'), 56.5 (C-3'), 22.3 (C-11), 22.2 (C-11'). HRESIMS: m/z 405.0621 ($[M-H]^-$ (calcd for $C_{22}H_{13}O_8$, 405.0610). See FIGS. 1F-1G.

These data revealed that compound 2 was 3-Hydroxy-diosquinone (3HDQ). The molecular ion, $[M-H]^-$, at m/z 405, 16 amu higher than that of DQ, indicated that 3HDQ contained additional oxygen functionality in its structure. See FIG. 1H. This new oxygen functionality was assigned as a hydroxyl group at C-3 and resonated upfield at δ 170.1 in its $^{13}$C NMR spectrum was confirmed by the absence of the proton signal at δ 6.85 in its $^1$H NMR spectrum when compared to the $^1$H NMR spectrum of DQ. See FIGS. 1F-1G.

Inhibitory Effects of DQ and 3HDQ on the Vegetative Growth of Wild-Type Strains *A. flavus* AF3357 and *A. parasiticus* SU-1, ATCC56775

DQ (5 mg) was dissolved in 200 μL of DMSO to make a stock solution (I) with a concentration of 0.025 mg/μL (w/v). Using this stock solution, five serial dilutions were carried out by taking 100 μL of stock solution I and mixing it with 100 μL of DMSO. Serial dilutions were conducted to make stock solutions II, III, IV, and V. From each stock solution, 10 μL were transferred into the test well plate (in triplicate for each stock solution) and 5 mL of GM S agar was poured into each test well while shaking gently to ensure homogeneous mixing of the contents in order to get concentrations 50, 25, 12.5, 6.25, and 3.125 μg/mL, respectively, as final concentrations in the test well plates. The highest concentration (100 μg/mL) was prepared by transferring 20 μL from the stock solution I into 5 mL GM S plate. Thus, dose levels applied for the inhibitory experiments were 100, 50, 25, 12.5, 6.25, and 3.125 μg/mL. The GM S agar medium was left to solidify in the test well plates before inoculation. Serial dilutions of 3HDQ were prepared in the same way that resulted in the same final concentrations of 100, 50, 25, 12.5, 6.25, and 3.125 μg/mL in the test well plates. *A. flavus* (AF3357) and *A. parasiticus* (SU-1, ATCC56775) were exposed to such DQ and 3HDQ by allowing them to grow on the surface of treated GM S growth medium (5 mL) in the test well plates. The plates that contained GMS only or GMS with DMSO only were the positive and negative controls, respectively. Six-well culture plates (SIAL0516, Sigma-Aldrich, St Louis, Mo. 63103, USA) were used throughout this study. Conidiospores ($1\times10^4$ CFU/plate) of each fungal strain were center-inoculated into each test well and incubated in the dark at 30° C. for 10 days. Fungal growth was estimated by measuring colony diameter in perpendicular directions for each colony every 24 h for 10 days. All colony diameter measurements were recorded as mean±standard error (SE) as previously described (Roze et al., 2011). The growth inhibition percentages were obtained by the following formula:

Growth Inhibition (%)=(Control−Treatment)/Control×100%

Estimation of Fungal Sporulation

After 10-day incubation in the dark at 30° C. on GM S medium, conidiospores of *A. flavus* (AF3357) and *A. parasiticus* (SU-1, ATCC56775) were harvested, and spore numbers in (CFU/plate) for each colony were estimated using a hemocytometer as described previously (Roze et al., 2004). Averages of spore numbers (CFU/plate) for each dose concentration were determined.

Extraction and Quantification of Aflatoxins from Growth Medium

Total aflatoxins in the growth medium and mycelia were extracted with 5 mL chloroform in 50 mL-Falcon tubes (Denville Scientific Inc. South Plainfield, N.J. 07080, USA). Chloroform (5 mL) was added to a 50 mL-Falcon tube containing the sample (chunks (@~6×6×5 mm) of solid medium agar from the test well plate). The chunks were vortexed for 5 s and the mixture allowed to rest for 10 min before withdrawing the extract into a 20-mL scintillation vial. This procedure was repeated three times and the extracts were dried completely under a stream of nitrogen gas, and each vial was reconstituted with 500 μL of 70% methanol (Roze et al., 2004). Five L of the reconstituted solution were dissolved in 1000 μL of 70% methanol, and the solution was vortexed for 30 s to obtain the final sample solution (pH=6.7). Then, total aflatoxin in the sample was quantified using Veratox® direct competitive enzyme-linked immunosorbent assay (ELISA) as described by the manufacturer (Neogen Corporation, Lansing Mich., USA). Averages of total aflatoxin (ng/plate) at each dose level were determined and recorded.

Statistical Analysis

Statistical analysis used Duncan's method for pairwise comparisons, which were performed using SigmaStat one-way analysis of variance (One-Way ANOVA) scientific statistical software, version 11.0 from Jandel Corporation, San Rafael, Calif., USA.

EXAMPLE 2

*D. mafiensis* Root Materials Screened Against *A. parasiticus* B62

This Example illustrates that *Diospyros mafiensis* root powders and extracts inhibit growth and production of norsolorinic acid (NA), as visual evidence of aflatoxin biosynthesis inhibition.

Figure 1B:
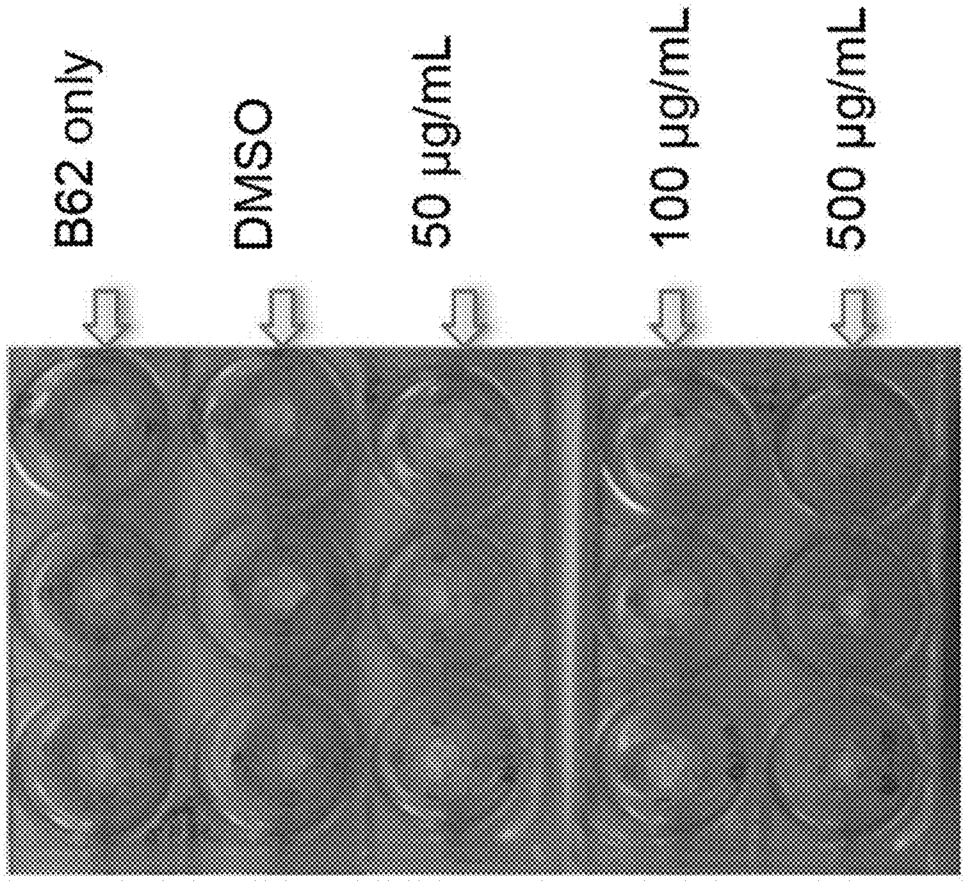
Figure 1C:
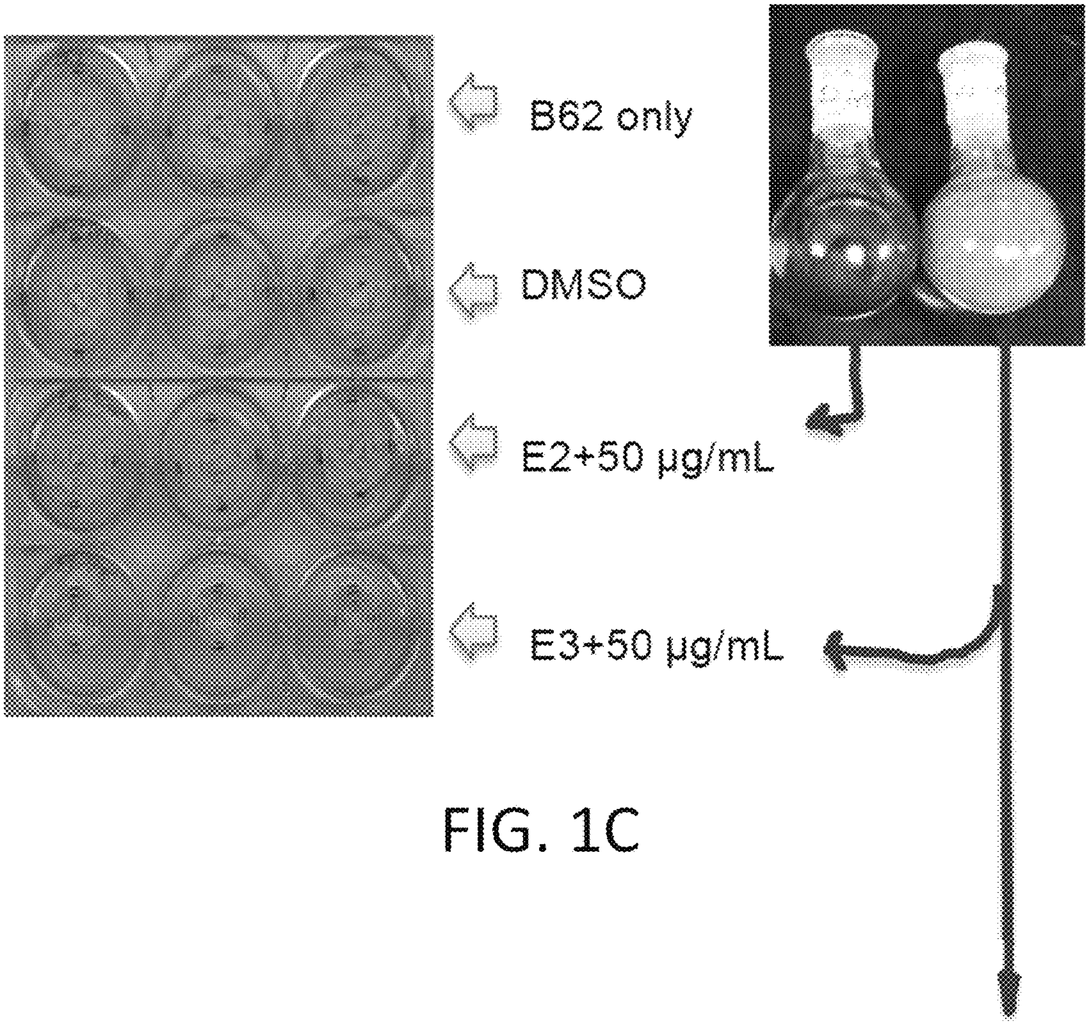

The root powders of *D. mafiensis* (R3) decreased vegetative growth and norsolorinic acid production by *A. parasiticus* B62 compared to the untreated control (FIG. 1A). Crude methanolic extracts of *D. mafiensis* root bark also effectively inhibited both vegetative growth and norsolorinic acid production of *A. parasiticus* (FIG. 1B). Vegetative growth and norsolorinic acid decreased drastically with increased doses of the extract from 50 to 500 μg/mL as compared to the controls (B62 only and DMSO).

EXAMPLE 3

Bioassay-Guided Extraction and Isolation

This Example illustrates extraction procedures and the activities of various types of extracts.

Extraction procedures described in the foregoing Examples (e.g, for *Diospyros mafiensis*) were employed. The oily fraction D weakly inhibited vegetative growth and norsolorinic acid production. However, fractions A, B, E, and F weakly inhibited vegetative growth but strongly inhibited norsolorinic acid production by *A. parasiticus* B62 in a dose-dependent manner. Fraction E exhibited the strongest activity against *A. parasiticus* B62 growth and norsolorinic acid production. Thus, fraction E was selected for further fractionation to obtain sub-fractions E1, E2, and E3. Sub-fraction E1 was inactive against the growth of *A. parasiticus* B62. Conversely, sub-fraction E2 inhibited *A. parasiticus* B62 vegetative growth more weakly than E3, but both were strong inhibitors of NA productions. Sub-fraction E3 was the most potent against the vegetative growth of *A. parasiticus.*

Figure 1D:
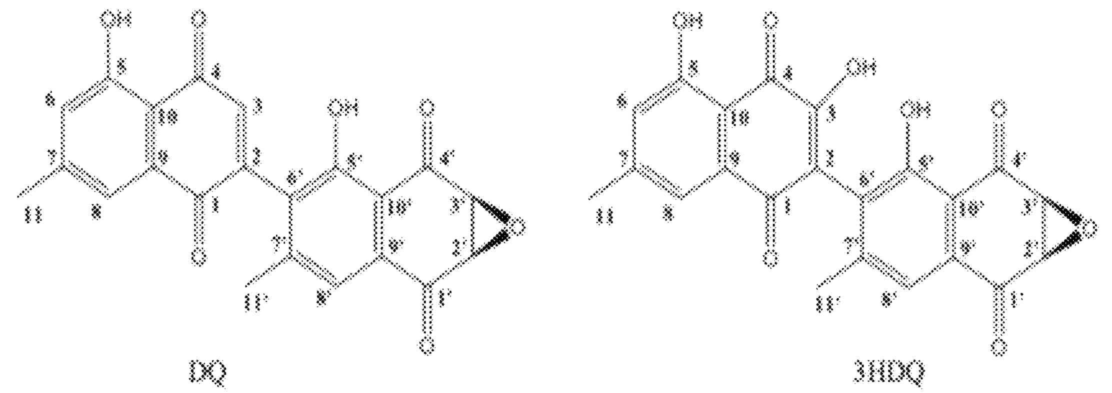
Figure 1E:
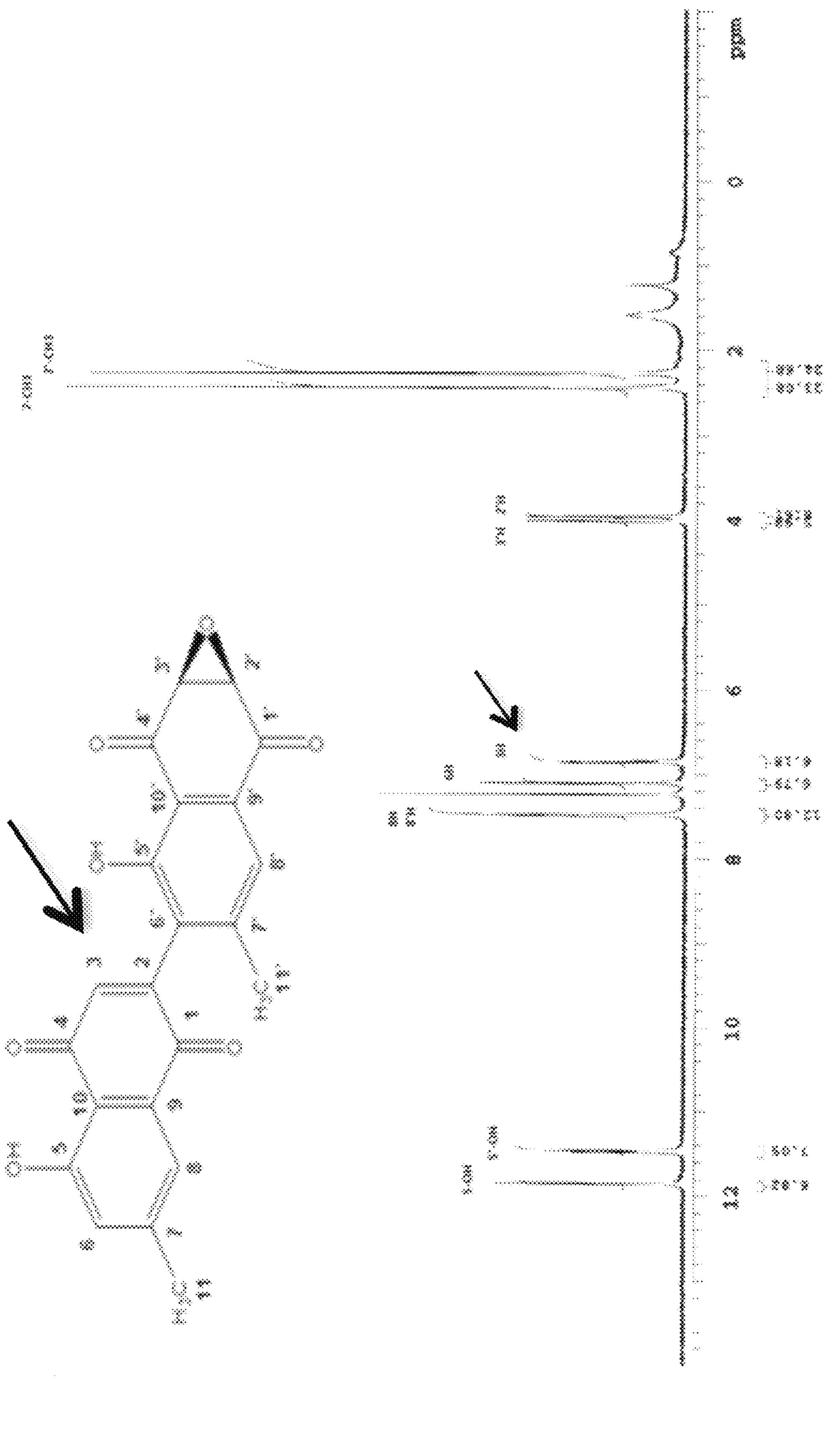
FIG. 1E shows a $^1$H NMR spectrum of diosquinone (DQ). The doublet at δ 6.18 ppm corresponds to a proton at carbon 3 position (see arrows). This was a diagnostic signal to identify its analogue 3HDQ in FIG. 1D.
Figure 1F:
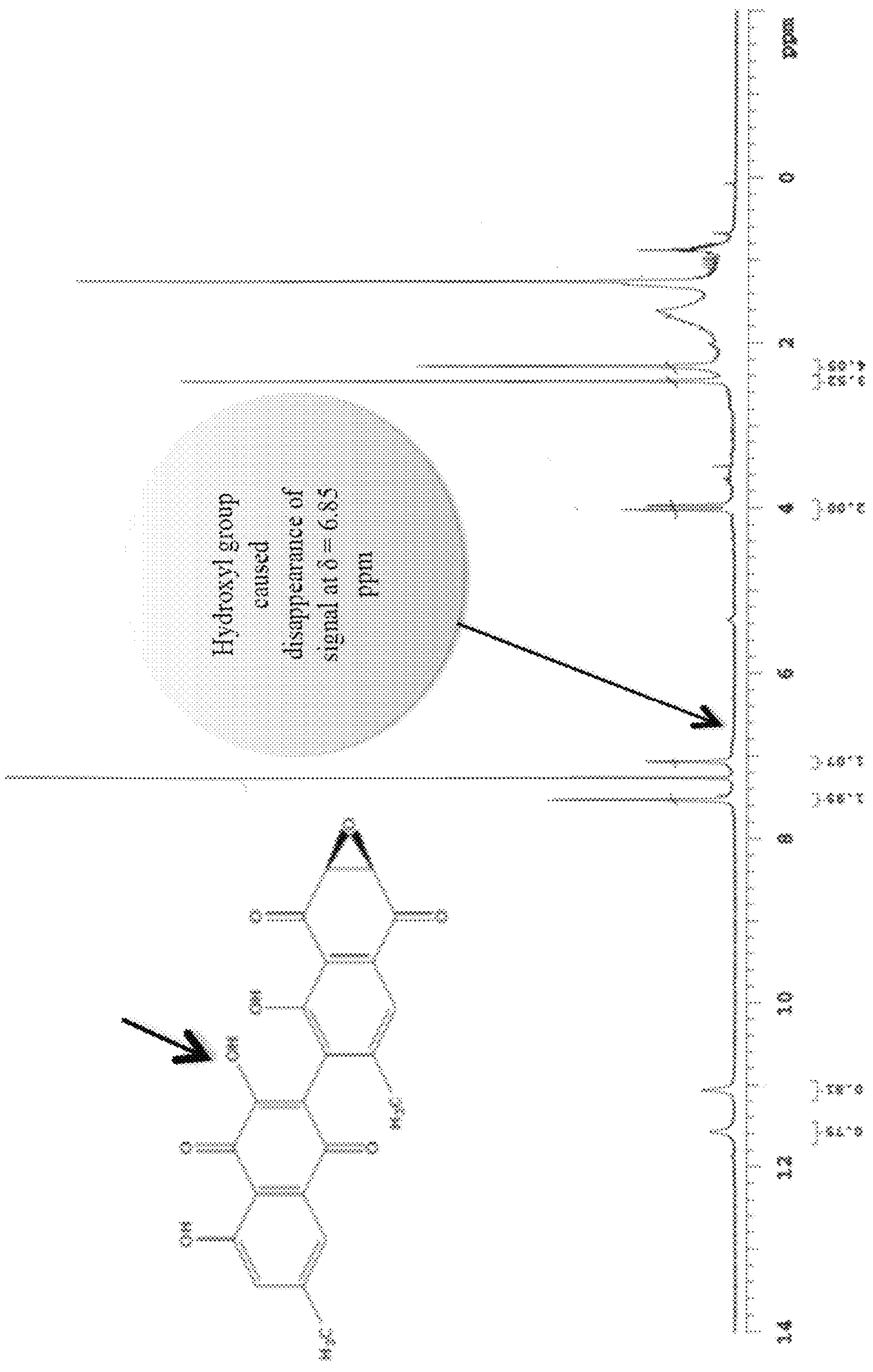
FIG. 1F shows a $^1$H NMR spectrum of 3-hydroxy diosquinone (3HDQ). The doublet at δ 6.85 ppm (see arrows) corresponds to a proton at carbon 3 position disappeared due to hydroxyl group. Compare FIG. 1F with FIG. 1E.
Figure 1G:
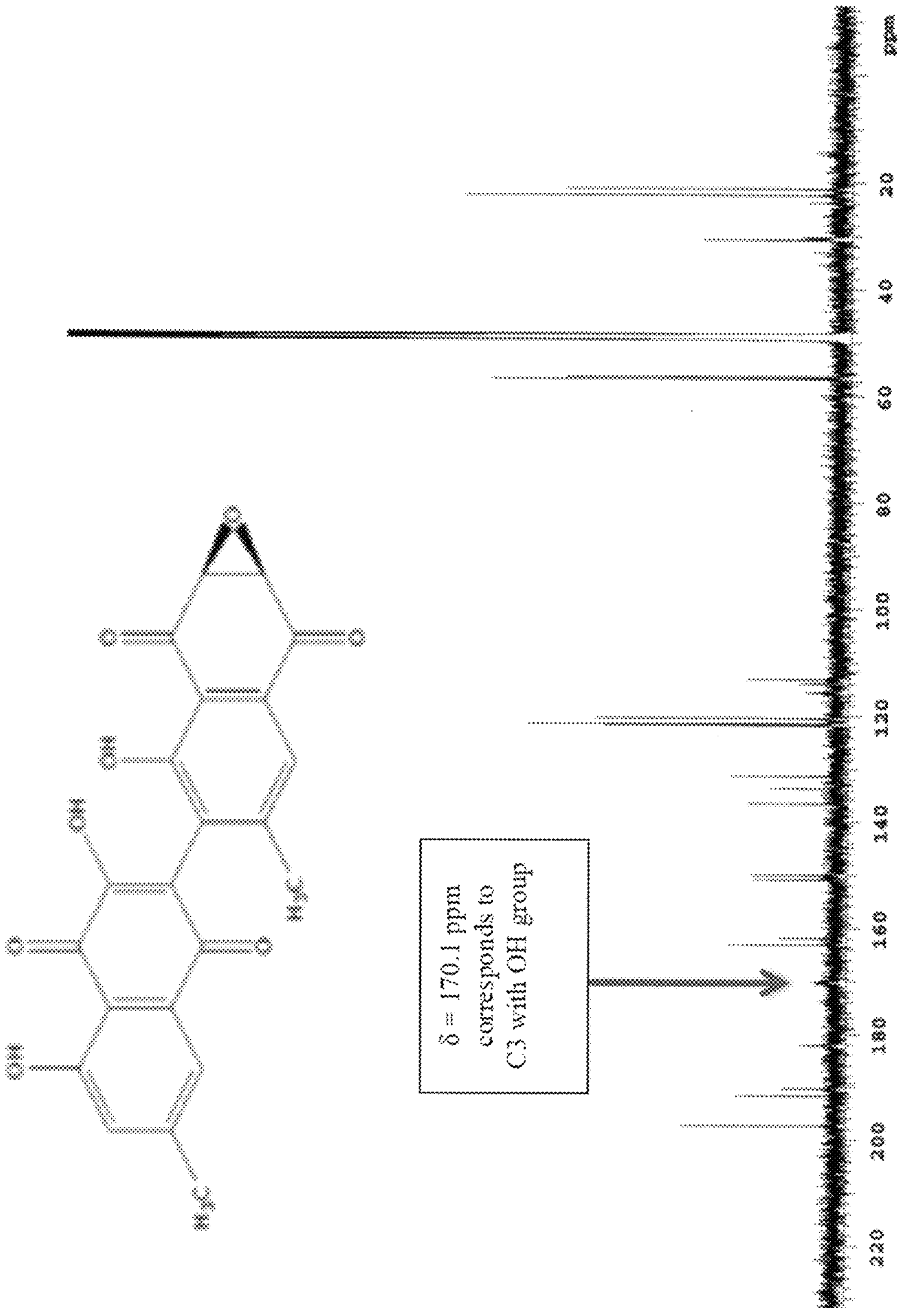
FIG. 1G shows a $^{13}$C-NMR Spectrum of 3HDQ, confirming the presence of hydroxyl group at carbon 3 position in 3HDQ.
Figure 1H:
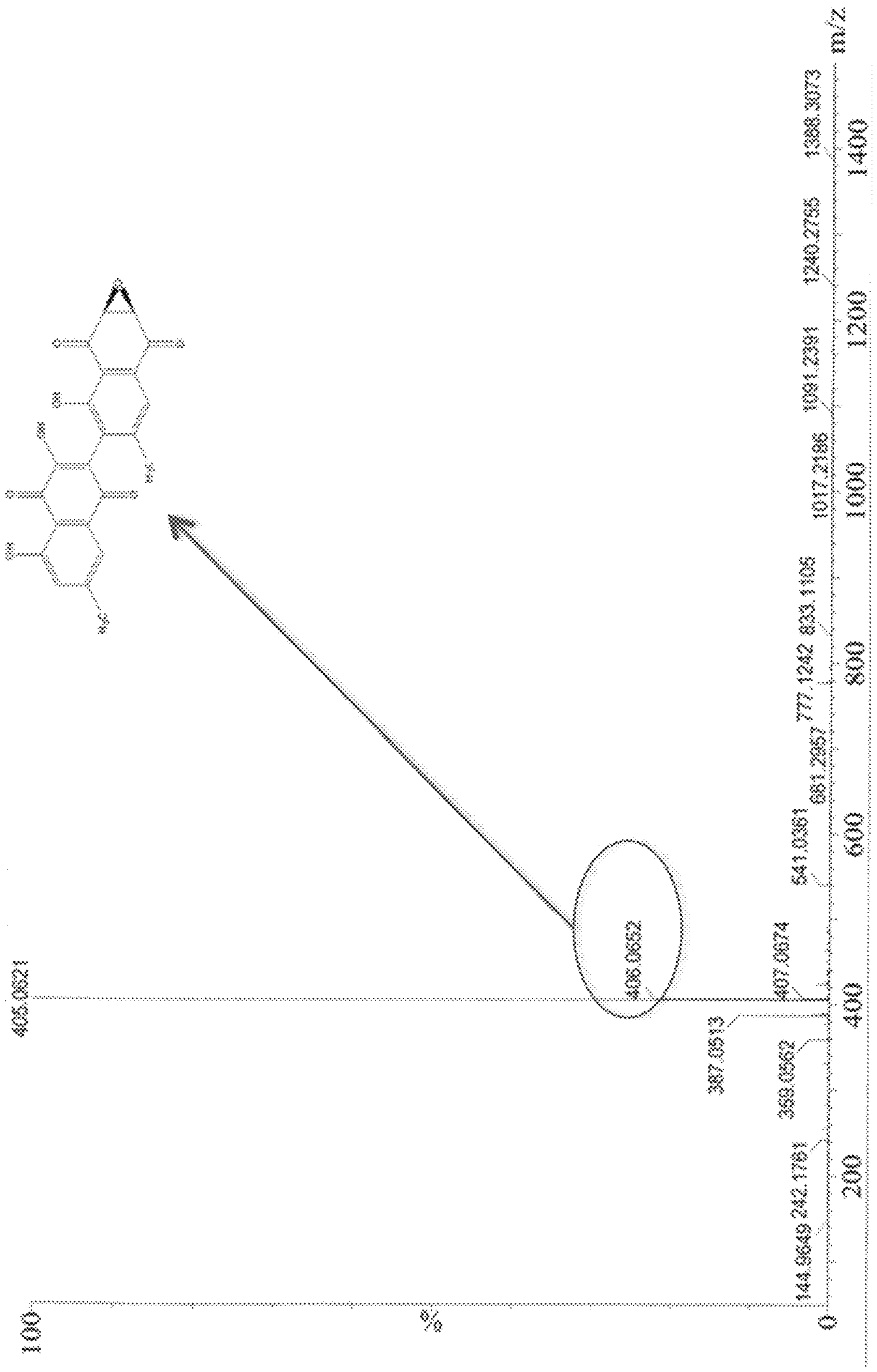
FIG. 1H shows a mass spectrum of 3HDQ, confirming the presence of a hydroxyl group at carbon 3 position. The difference in molar masses of the two analogs (DQ from 3HDQ) is 16 amu, which indicated that there is additional oxygen functionality in 3HDQ relative to DQ.

Two bioactive compounds were isolated, purified, characterized from the E3 subfraction, and identified as Diosquinone (DQ) and 3-Hydroxydiosquinone (3HDQ) (FIG. 1C-1D). The spectral data of DQ were in agreement with Khan & Rwekika (Phytochemistry 50: 143-146 (1999)) who first isolated and characterized it from *D. mafiensis*. The spectral data of a new analog of DQ, 3-hydroxy diosquinone (3HDQ), are reported here.

EXAMPLE 4

Synthesis of Diosquinone (DQ) and 3-Hydroxydiosquinone (3HDQ)

This Example illustrates methods for synthesizing diosquinone (DQ) and 3-hydroxy diosquinone (3HDQ).

Synthetic scheme I illustrates a synthetic method for making compound 1, diosquinone (DQ).

Scheme I

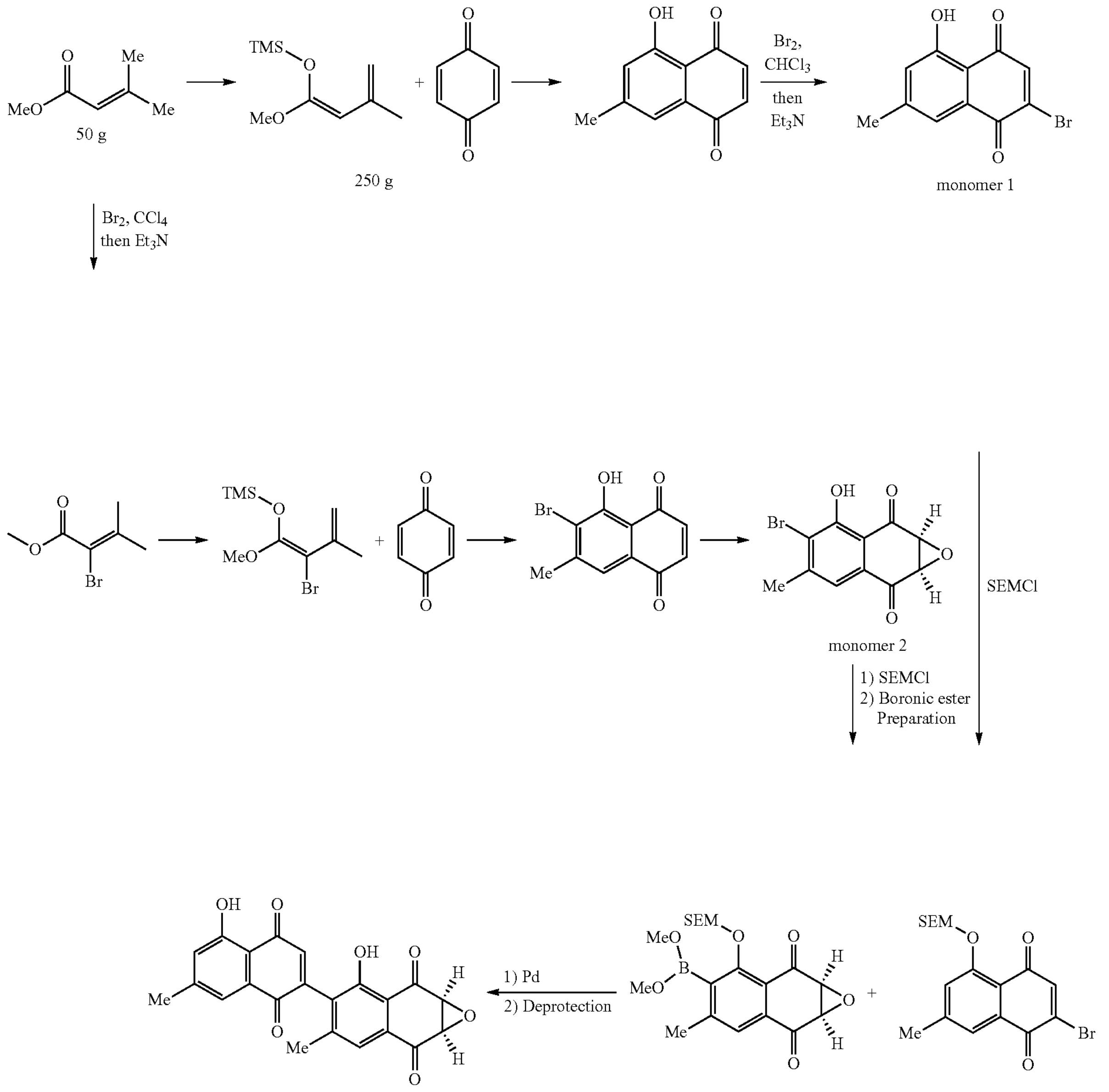

Compound 1

Synthetic scheme II illustrates a synthetic method for making compound 2, 3-hydroxy diosquinone (3HDQ).

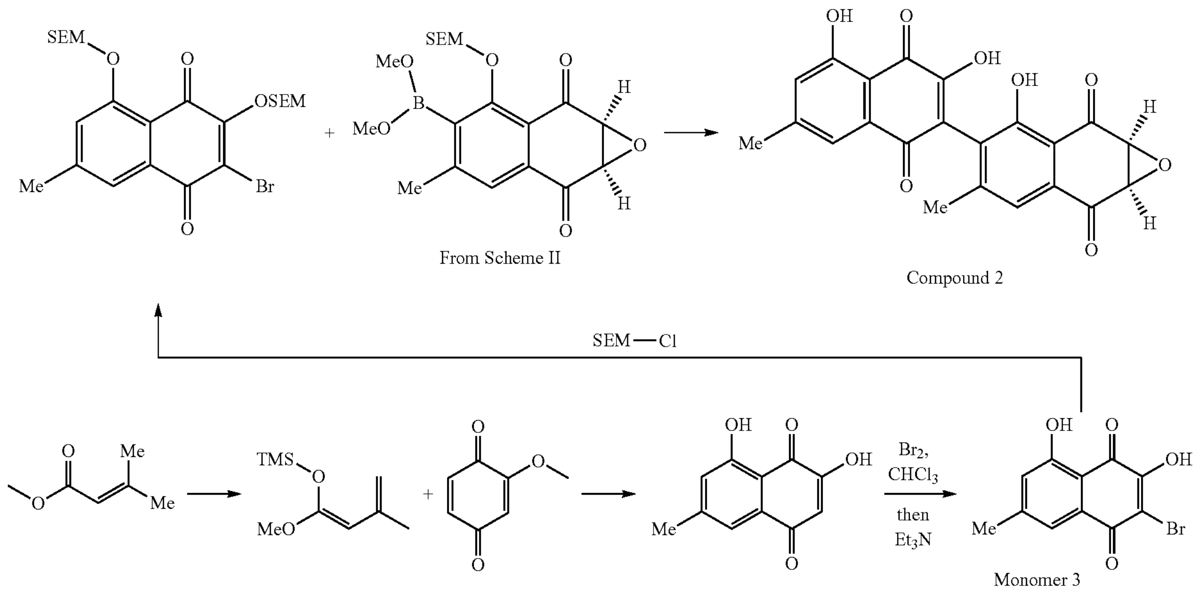

EXAMPLE 5

Inhibitory Effects of DQ and 3HDQ on the Vegetative Growth of Wild-Type Strains *A. flavus* AF3357 and *A. parasiticus* SU-1 (ATCC56775)

This Example illustrates the inhibitory properties of Diosquinone (DQ) and 3-Hydroxydiosquinone (3HDQ).

Figure 2A:
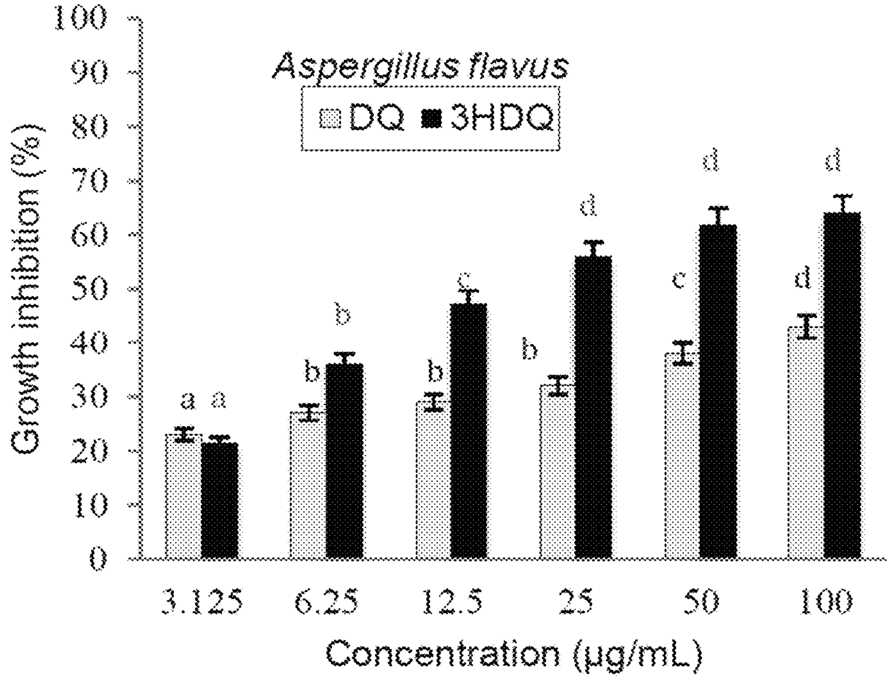
FIG. 2A-2F illustrates the inhibitory effects of diosquinone (DQ) and 3-hydroxy diosquinone (3HDQ) on fungal vegetative growth.
Figure 2B:
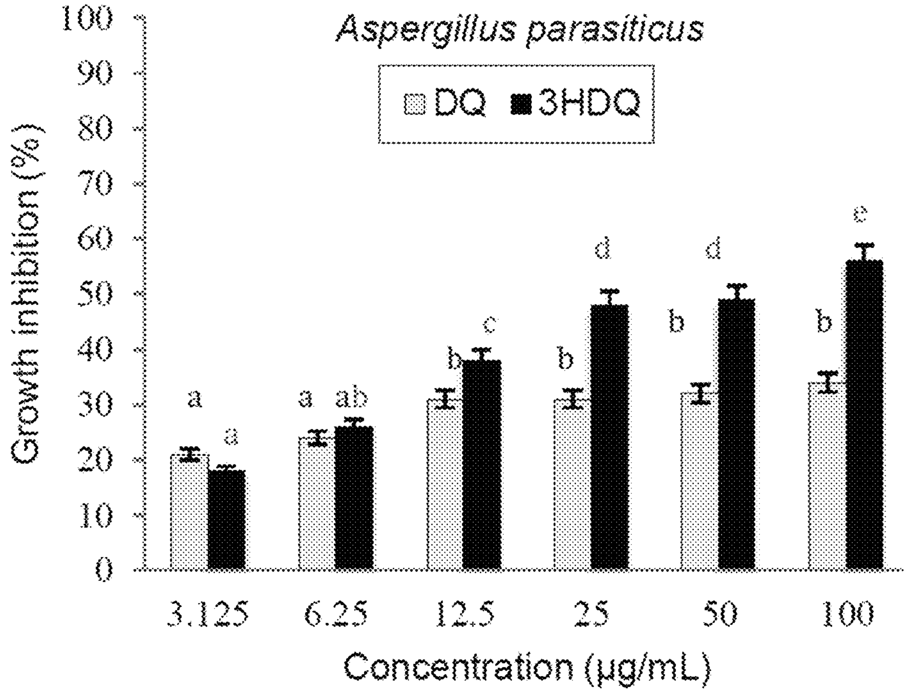

FIGS. 2A-2B illustrate the growth inhibitory effects of DQ and 3HDQ assessed at concentrations, ranging from 3.125 to 100 μg/mL on *A. flavus* and *A. parasiticus* grown on glucose minimal salts (GM S) for 10 day s. At the highest concentration (100 μg/mL), DQ weakly but significantly inhibited ($p<0.05$) *A. flavus* (43%) and *A. parasiticus* (34%) growth when compared with the control. There was no change in the level of inhibition of vegetative growth of *A. parasiticus* by DQ from 12.5 to 100 μg/mL. The 50 percent minimum inhibitory concentration ($MIC_{50}$) values of DQ in *A. flavus* and *A. parasiticus* were all greater than 100 μg/mL.

In contrast, at the highest concentration (100 μg/mL), 3HDQ significantly ($p<0.05$) inhibited the vegetative growth of *A. flavus* (64%) and *A. parasiticus* (56%). No significant difference in inhibition of vegetative growth of *A. flavus* was observed by 3HDQ from 25 to 100 μg/mL. The $MIC_{50}$ values for 3HDQ were 14.9 μg/mL on *A. flavus* and 39.1 μg/mL on *A. parasiticus* (FIGS. 2A and 2B, respectively). Vegetative growth of *A. flavus* was more susceptible to DQ and 3HDQ than *A. parasiticus*. Significantly, 3HDQ was more potent for both *A. flavus* and *A. parasiticus* than DQ especially at doses greater than 6.25 μg/mL (FIGS. 2A and 2B).

Of particular interest, 100 μg/mL of DQ caused a complete loss of green pigmentation in colonies of *A. flavus* while a similar dose of 3HDQ did not cause loss of greenish pigmentation in the colonies of the same fungus suggesting that DQ at doses ≥100 μg/mL exerts morphological alterations and disrupts ability to form pigments. This phenomenon was not observed in *A. parasiticus* because it did not form greenish pigmentation at all doses.

EXAMPLE 6

Impact of DQ and HDQ on Fungal Sporulation

This Example illustrates the effects of Diosquinone (DQ) and 3-Hydroxydiosquinone (3HDQ) on fungal sporulation.

Figure 2C:
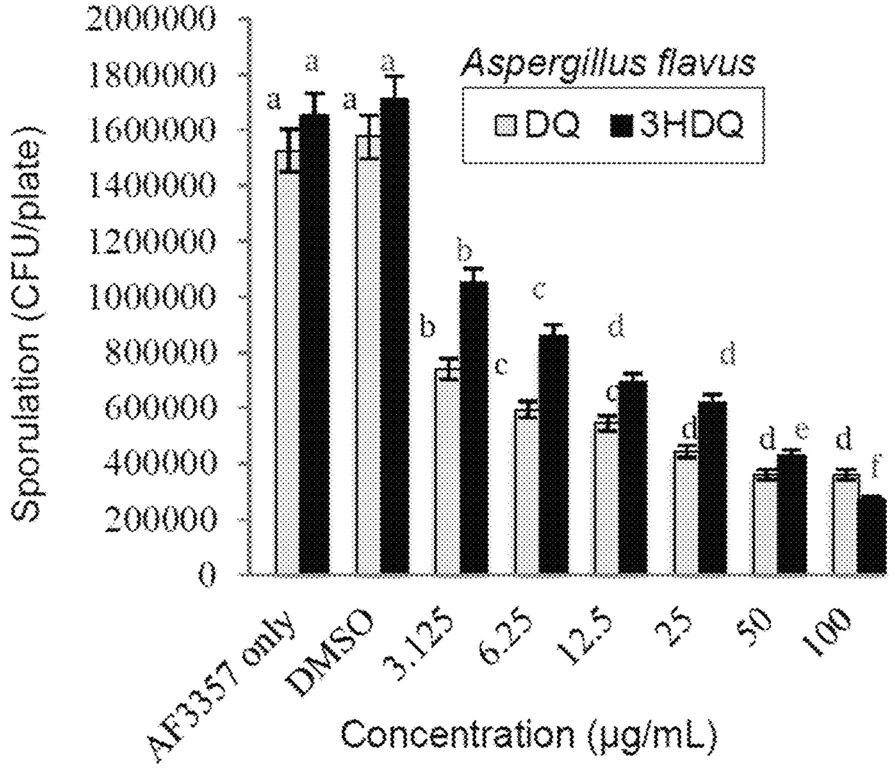
Figure 2D:
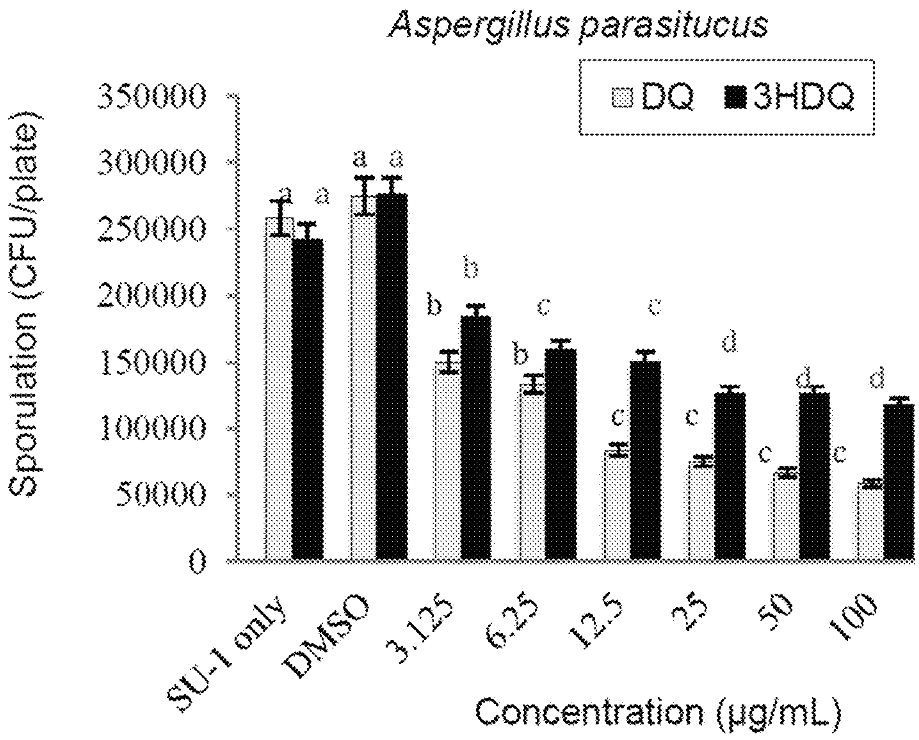

Conidiospore number for both *A. flavus* (A) and *A. parasiticus* mold strains decreased significantly ($p<0.05$) in a dose-dependent manner when they were exposed to increasing doses of DQ and 3HDQ as compared with the controls (FIGS. 2C and 2D). For example, 100 μg/mL of 3HDQ strongly decreased conidiospore numbers from $1.7\times10^6$ (control AF3357) to $2.7\times10^5$ spores/plate (98% reduction of sporulation) in *A. flavus* after 10 days of growth (FIG. 2C). By comparison, 100 μg/mL of 3HDQ was less effective in decreasing conidiospore number from $2.4\times10^5$ in control SU-1 to $1.2\times10^5$ spores/plate (52% reduction of sporulation) in *A. parasiticus* grown for 10 days (FIG. 2D). In contrast, DQ was equally potent at reducing conidiospore number in both fungal strains after exposure to 100 μg/mL for 10 days of incubation. DQ reduced conidiospore number from $1.5\times10^6$ in control AF3357 to $3.6\times10^5$ spores/plate (76% reduction of sporulation) in *A. flavus* (FIG. 2C) exposed to DQ for 10 days and decreased conidiospore number in *A. parasiticus* from $2.6\times10^5$ in control SU-1 to $5.8\times10^4$ sp ores/plate (77% reduction of sporulation) (FIG. 2D) after exposure for 10 day s. Overall, 3HDQ (with the exception of the 100 μg/mL dose) exhibited lower ability to reduce conidiospore number in both fungi than its counterpart DQ. This suggests that although the DQ was a weaker inhibitor of radial growth (FIG. 2B), it reduced conidiospore number more effectively.

EXAMPLE 7

Quantification of Total Aflatoxins Extracted from Growth Medium

This Example illustrates quantification of aflatoxins in culture media of *A. flavus* and *A. parasiticus* after culturing with diosquinone (DQ) or 3-hydroxy diosquinone (3HDQ).

Figure 2E:
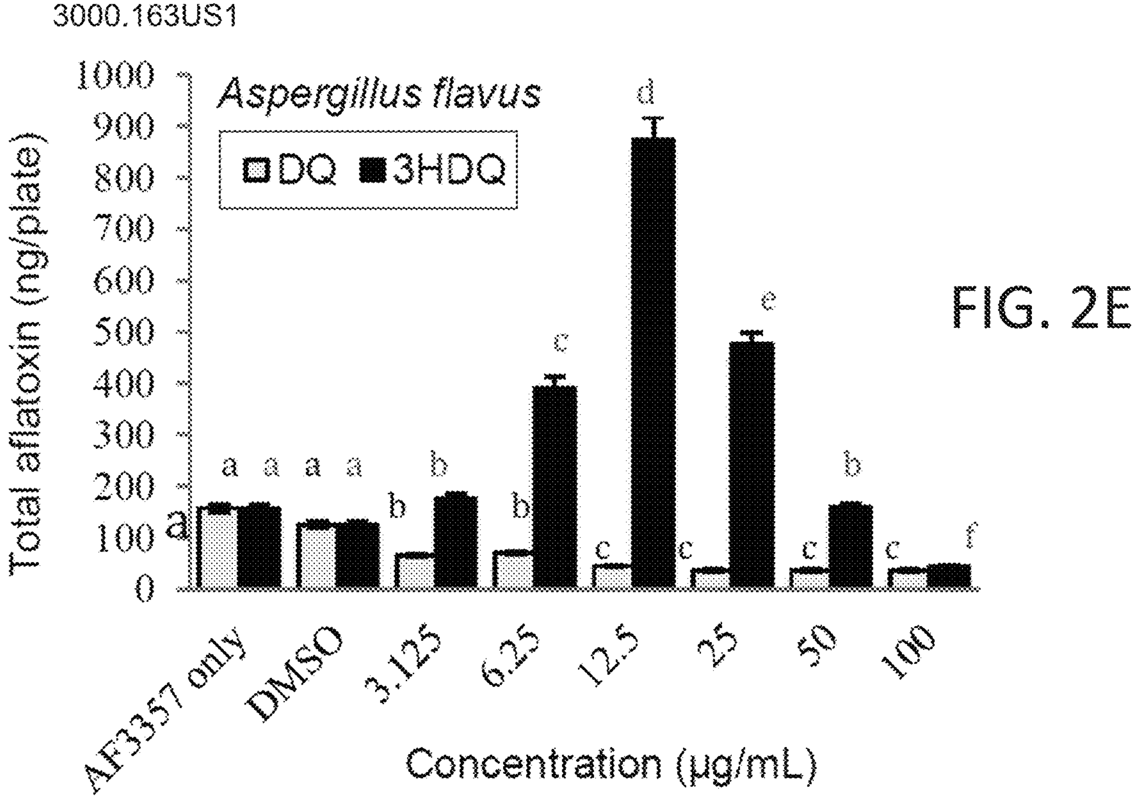
Figure 2F:
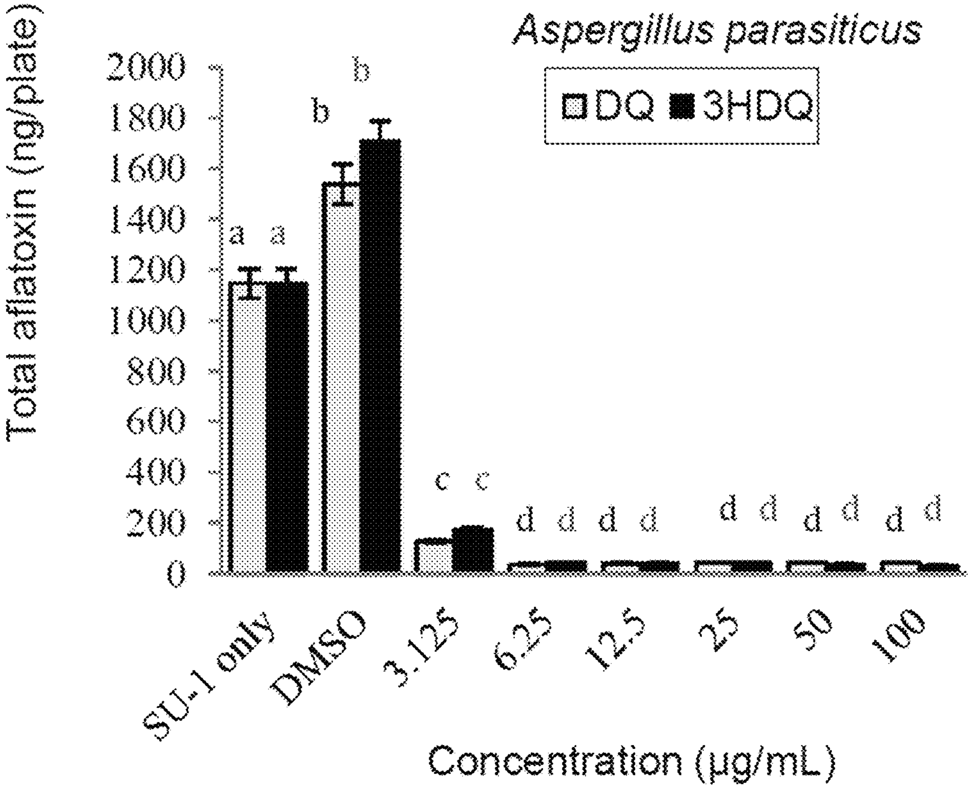
Figure 3A:
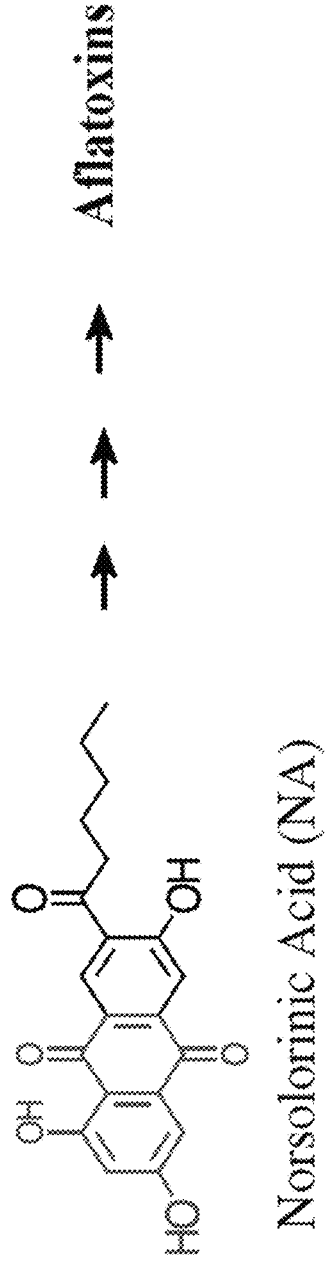
FIG. 3A-3B illustrate the process by which aflatoxins are generated from norsolorinic acid and potential modes of action of diosquinone (DQ) and 3-hydroxy diosquinone (3HDQ).
Figure 3B:
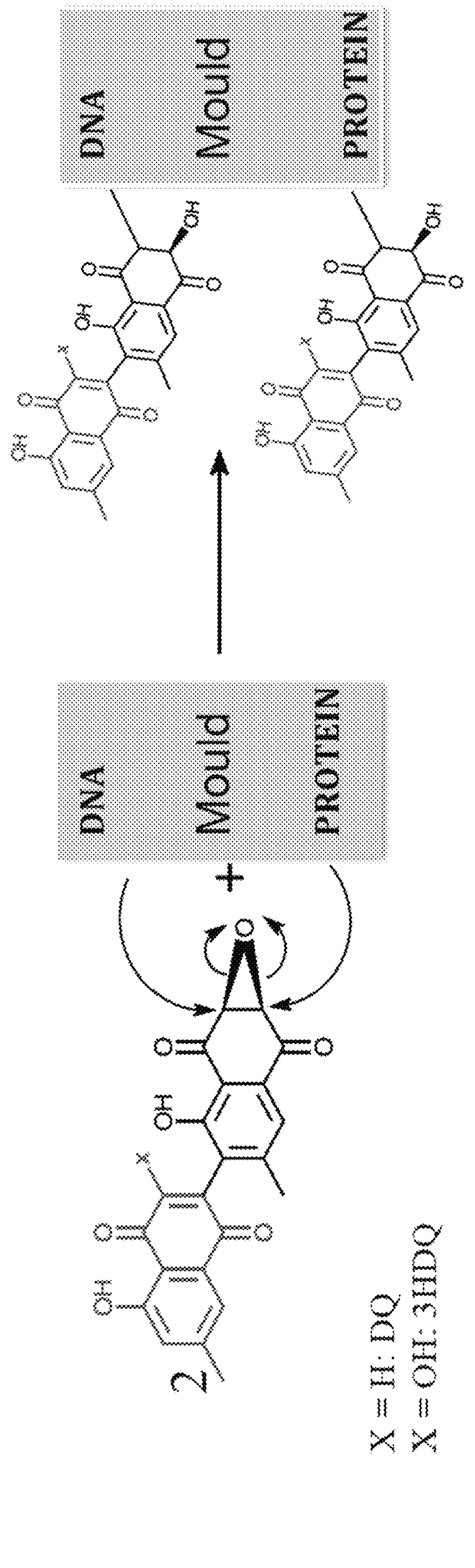

After incubation of center-inoculated *A. flavus* and *A. parasiticus* strains in the dark at 30° C. for 10 d, total aflatoxins were extracted from each plate containing growth media. FIGS. 2E and 2F show total aflatoxins (ng/plate) presented as mean±SE of three independent plates for each treatment group against two different wild-type fungal strains. Compared with the control (AF 3357 only), DQ significantly ($p<0.05$) inhibited aflatoxin production by *A. flavus* at all concentrations after 10 days and total aflatoxin accumulation was inversely proportional to an increase in dose (FIG. 2E). Higher doses (25 to 100 μg/mL) of DQ inhibited total aflatoxin accumulation by 77.2% (36 ng/plate in the treatment group compared with 157 ng/plate in the control, AF3357 only (FIG. 2E). In contrast, doses consisting of 3.125, 6.25, 12.5, 25, and 50 μg/mL of 3HDQ significantly promoted total aflatoxin production by *A. flavus* to the following amounts 176.5, 393.0, 872.4, 475.9, and 158.8 ng/plate, respectively, compared with 157.1 ng/plate in the control (AF3357 only). Significant inhibition of total aflatoxin production was observed at 100 μg/mL, which caused a 72% reduction of total aflatoxin from 157 ng/plate in the control (AF3357 only) to 43.5 ng/plate (FIG. 2E). DQ and 3HDQ inhibited total aflatoxin production by *A. parasiticus* at nearly equal efficacy (FIG. 2F). Compared with 1145.3 ng/plate total aflatoxin in the untreated control (SU-1 only), doses ≥6.25 μg/mL of DQ or HDQ nearly eliminated aflatoxin accumulation (44.7 ng/plate, 96.1% aflatoxin reduction; and 32.3 ng/plate, 97.2% aflatoxin reduction, respectively.

REFERENCES

Alejandra, M., Soledad, N., Etcheverry, M., 2013. Antifungal and antiaflatoxigenic activity by vapor contact of three essential oils, and effects of environmental factors on their efficacy. LWT—Food Science Technology 53(2): 434-444. DOI:10.1016/j.lwt.2013.03.012.

Alexander-Lindo, R. L., Morrison, E. Y. S. A., Nair, M. G., 2004. Hypoglycaemic effect of stigmast-4-en-3-one and its corresponding alcohol from the bark of *Anacardium occidentale* (cashew). Phytotherapy Research, 18(5): 403-407. doi:10.1002/ptr.1459.

Bluma, R., Amaiden, M. R., Etcheverry, M., 2008. Screening of Argentine plant extracts: Impact on growth parameters and aflatoxin B1 accumulation by *Aspergillus* Section Flavi. International Journal of Food Microbiology 122(1-2): 114-125. DOI:10.1016/j.ijfoodmicro.2007.11.050.

Bluma, R. V., Etcheverry, M. G., 2008. Application of essential oils in maize grain: Impact on *Aspergillus* Section Flavi growth parameters and aflatoxin accumulation. Food Microbiology 25(2): 324-334. DOI:10.1016/j.fm.2007.10.004.

Chanda, A., Roze, L. V., Kang S., Artymovich, K., Hicks, G. R., Raikhel, N. V, . . . Linz, J. E., (2009). A key role for vesicles in fungal secondary metabolism. *Proceedings of the National Academy of Sciences of the United States of America* 106(46): 19533-19538. DOI:10.1073/pnas.0907416106.

Chang P. K., Cary, J. W., Yu, J., Bhatnagar, D., Cleveland, T. E., 1995. *Aspergillus parasiticus* pksA, a homolog of *Aspergillus nidulans* wA, is required for aflatoxin $B_1$ biosynthesis. Molecular General Genetics 248: 270-277.

da Cruz Cabral, L., Fernández Pinto, V., Patriarca, A., 2013. Application of plant derived compounds to control fungal spoilage and my cotoxin production in foods. International Journal of Food Microbiology 166(1): 1-14. DOI:10.1016/j.ijfoodmicro.2013.05.026.

Denning D. W., Pleuvry, A., Cole, D. C., 2013. Global burden of allergic bronchopulmonary aspergillosis with asthma and its complication chronic pulmonary aspergillosis in adults. Medical Mycology 51(4): 361-370. DOI:10.3109/13693786.2012.738312.

El-Nagerabi, S. A. F., Elshafie, A. E., AlKhanjari, S. S., Al-Bahry, S. N., Elamin, M. R., 2013. Biological activities of *Boswellia sacra* extracts on the growth and aflatoxins secretion of two aflatoxigenic species of *Aspergillus* species. Food Control 34(2): 763-769. DOI: 10.5539/jfr.v2n3p93.

Fajardo, J. E., Waniska, R. D., Cuero, R. G., Pettit, R. E., 1995. Phenolic compounds in peanut seeds-enhanced elicitation by chosen and effects on growth and aflatoxin $B_1$ production by *Aspergillus flavus*. Food Biotechnology 9: 59-78.

Fanelli, C., Fabbri, A. A., 1989. Relationship between lipids and aflatoxin biosynthesis. Mycopathologia, 107(2-3): 115-120. DOI:10.1007/BF00707547.

Farag R. S., Daw, Z. Y., Aboraya, S. H., 1989. Influence of some spice essential oils on *Aspergillus parasiticus* growth and production of aflatoxins in a synthetic medium. Journal of Food Science 54(1): 74-76.

Fung D.Y.C., Taylor, S. U. E., Kahan, J., 1977. Effects of butylated hydroxyanisole (BHA) and butylated hydroxytoluene(BHT) on growth and aflatoxin production of *Aspergillus flavus*. Journal of Food Safety 1(1): 39-51. DOI:10.1111/j.1745-4565.1977.tb00258.x.

Gafner, F., Chapuis, J. C., Msonthi, J. D., Hostettmann, K., 1987. Cytotoxic naphthoquinones, molluscicidal saponins and flavonols from *Diospyros zombensis*. Phytochemistry 26(9): 2501-2503. DOI:10.1016/S0031-9422(00)83864-9.

Georges, K., Jayaprakasam, B., Dalavoy, S. S., Nair, M. G., 2008. Pest-managing activities of plant extracts and anthraquinones from *Cassia nigricans* from Burkina Faso. Bioresource Technology, 99(6): 2037-2045. doi:10.1016/j.biortech.2007.02.049.

Grintzalis, K., Vernardis, S. I., Klapa, M. I., Georgiou, C. D., 2014. Role of oxidative stress in sclerotial differentiation and aflatoxin $B_1$ biosynthesis in *Aspergillus flavus*. Applied Environmental Microbiology 80(18): 5561-5571. DOI:10.1128/AEM.01282-14.

Hall, J. B., Rodgers, W. A., 1986. Pole cutting pressure in Tanzanian forest. Forest Ecology and Management 14: 133-140.

Hamza, O. J. M., van den Bout-van den Beukel, C. J. P., Matee, M. I. N., Moshi, M. J., Mikx, F. H. M., Selemani, H. O., . . . Verweij, P. E., 2006. Antifungal activity of some Tanzanian plants used traditionally for the treatment of fungal infections. Journal of Ethnopharmacology 108(1): 124-32. DOI:10.1016/j.jep.2006.04.026.

Hell, K., Cardwell, K., Setamou, M., Schulthess, F., 2000. Influence of insect infestation on aflatoxin contamination of stored maize in four agroecological regions in Benin. African Entomology 8(1991): 1-9. DOI: 10.1016/S0022-474X (99)00056-9.

Herath, W. H. M. W., Rajasekera Nimal, D. S., Sultanbawa, M. U. S., Wannicama, G. P., Balasubramaniam, S., 1978. Triterpenoid, coumarin and quinone constituents of eleven *Diospyros* species (Ebenaceae). Phytochemistry, 17: 1007-1009.

Holmes, R. A., Boston, R. S., Payne, G. A., 2008. Diverse inhibitors of aflatoxin biosynthesis. Applied Microbiology and Biotechnology 78(4): 559-572. DOI:10.1007/s00253-008-1362-0.

Iyer, R. S., Voehler, M. W., Harris, T. M., 1994. Adenine adduct of aflatoxin $B_1$ epoxide. Journal of American Chemical Society 116(20): 1360-1364.

Jayashree, T., Subramanyam, C., 1999. Antiaflatoxigenic activity of eugenol is due to inhibition of lipid peroxidation. Letters in Applied Microbiology 28(3): 179-183. DOI:10.1046/j.1365-2672.1999.00511.x.

Jiang Y., Jolly, P. E., Preko, P., Wang J. S., Ellis, W. O., Phillips, T. D., Williams, J. H., 2008. Aflatoxin-related immune dysfunction in health and in human immunodeficiency virus disease. Clinical & Developmental Immunology 2008, 790309. DOI:10.1155/2008/790309.

Juglal, S., Govinden, R., Odhav, B., 2002. Spice oils for the control of co-occurring mycotoxin-producing fungi. Journal of Food Protection 65(4): 683-687.

Kedia, A., Prakash, B., Mishra, P. K., Dubey, N. K., 2014. Antifungal and antiaflatoxigenic properties of *Cuminum cyminum* (L.) seed essential oil and its efficacy as a preservative in stored commodities. International Journal of Food Microbiology 168-169: 1-7. DOI:10.1016/j.ijfoodmicro.2013.10.008.

Khan, M. R., Nkunya, M. H., Weavers, H., 1980. Triterpenoids from leaves of *Diospyros* species. Planta Medica 38: 308.

Khan, M. R., Rwekika, E., 1999. 6", 8' Bisdiosquinone from *Diospyros mafiensis*. Phytochemistry 50: 143-146.

Khlangwiset, P., Shephard, G. S., Wu, F., 2011. Aflatoxins and growth impairment: A review. Critical Reviews in Toxicology, 41(January), 740-755. DOI: 10.3109/10408444.2011.575766.

Kuete, V., Tangnouo, J. G., Marion Meyer, J. J., Lall, N., 2009. Diospyrone, crassiflorone and plumbagin: three antimycobacterial and antigonorrhoeal naphthoquinones from two *Diospyros* spp. International Journal of Antimicrobial Agents 34(4): 322-325. DOI:10.1016/j.ijantimicag.2009.04.008.

Lajubutu, B. A., Pinney, R. J., Roberts, M. F., Odelola, H. A., Oso, B. A., 1995. Antibacterial activity of diosquinone and plumbagin from the root of *Diospyros mespiliformis* (Hostch) (Ebenaceae). Phytotherapy Research 9(5): 346-350. DOI:10.1002/ptr.2650090508.

Lee, L. S., Bennett, J. W., Goldblatt, L. A., Lundin, R. E., 1971. Norsolorinic acid from a mutant strain of *Aspergillus parasiticus*. Journal of American Oil Chemists Society 48(2): 93-94. Retrieved from http://www.ncbi.nlm.nih.gov/pubmed/5546372.

Liu, Y., Wu, F., 2010. Global burden of aflatoxin-induced hepatocellular carcinoma: a risk assessment. Environmental Health Perspectives 118(6): 818-824. DOI:10.1289/ehp.0901388.

Mallavadhani, U. V., Panda, A. K., Rao, Y. R., 1998. Pharmacology and chemotaxonomy of *Diospyros*. Phytochemistry 49(4): 901-951. DOI:10.1016/S0031-9422(97)01020-0.

Marston A, Msonthi J D, Hostettmann K., 1984. Naphthoquinones of *Diospyros usambarensis*; their molluscicidal and fungicidal activities. Planta Medica 50: 279.

Moshi, M. J., Mbwambo, Z. H., 2002. Experience of Tanzanian traditional healers in the management of non-insulin dependent diabetes mellitus. Pharmaceutical Biology 40(7): 552-560. DOI:10.1076/phbi.40.7.552.14691.

Pfaller, M. A., Pappas, P. G., Wingard, J. R., Pfaller, M. A., Pappas, P. G., Wingard, J. R., 2016. Invasive current fungal pathogens: Epidemiological trends. Epidemiology of invasive mycoses—CID 2006:43 (Suppl 1): S3-14.

Prakash, B., Mishra, P. K., Kedia, A., Dubey, N. K., 2014. Antifungal, antiaflatoxinic and antioxidant potential of chemically characterized *Boswellia carterii* Birdw essential oil and its in vivo practical applicability in preservation of *Piper nigrum* L. fruits. LWT—Food Science Technology 56(2): 240-247. DOI:10.1016/j.lwt.2013.12.023.

Prakash, B., Shukla, R., Singh, P., Kumar, A., Mishra, P. K., Dubey, N. K., 2010. Efficacy of chemically characterized *Piper betle* L. essential oil against fungal and aflatoxin contamination of some edible commodities and its antioxidant activity. International Journal Food Microbiology 142: 114-119.

Reverberi, M., Zjalic, S., Ricelli, A., Fabbri, A. A., Fanelli, C., 2006. Oxidant/antioxidant balance in *Aspergillus parasiticus* affects aflatoxin biosynthesis. Mycotoxin Research 22(1): 39-47.

Roze, L. V., Laivenieks, M., Hong S. Y., Wee, J., Wong S. S., Vanos, B., . . . Linz, J. E., 2015. Aflatoxin biosynthesis is a novel source of reactive oxygen species-A potential redox signal to initiate resistance to oxidative stress? *Toxins* 7(5): 1411-1430. DOI: 10.3390/toxins7051411.

Roze, L. V., Beaudry, R. M., Arthur, A. E., Calvo, A. M., Linz, J. E., 2007. Aspergillus volatiles regulate aflatoxin synthesis and asexual sporulation in *Aspergillus parasiticus*. Applied and Environmental Microbiology 73(22): 7268-7276. DOI: 10.1128/AEM.00801-07.

Roze, L. V., Calvo, A. M., Gunterus, A., Beaudry, R., Kall, M., Linz, J. E., 2004. Ethylene modulates development and toxin biosynthesis in *aspergillus* possibly via an ethylene sensor-mediated signaling pathway. Journal of Food Protection 67(3): 438-447.

Roze, L. V., Chanda, A., Linz, J. E., 2011. Compartmentalization and molecular traffic in secondary metabolism: A new understanding of established cellular processes. Fungal Genetic Biology 48(1): 35-48. DOI:10.1016/j.fgb.2010.05.006.

Roze, L. V., Koptina, A. V., Laivenieks, M., Beaudry, R. M., Jones, D. A., Kanarsky, A. V., Linz, J. E., 2011. Willow volatiles influence growth, development, and secondary metabolism in *Aspergillus parasiticus*. Applied Microbiology and Biotechnology 92(2): 359-370. DOI: 10.1007/s00253-011-3339-7.

Strosnider, H., Azziz-Baumgartner, E., Banziger, M., Bhat, R. V., Breiman, R., Brune, M. N., . . . Wilson, D., 2006. Workgroup report: Public health strategies for reducing aflatoxin exposure in developing countries. Environmental Health Perspectives 114(12):1898-1903. DOI: 10.1289/ehp.9302.

Tice, G., Buchanan, R. L., 1981. Regulation of aflatoxin biosynthesis: Effect of exogenously supplied cyclic nucleotides. Journal of Food Science 47: 153-157.

Velazhahan, R., Vijayanandraj, S., Vijayasamundeeswari, A., Paranidharan, V., Samiyappan, R., Iwamoto, T., . . . Muthukrishnan, S., 2010. Detoxification of aflatoxins by seed extracts of the medicinal plant, Trachyspermum-ammi (L.) Sprague ex Turrill—Structural analysis and biological toxicity of degradation product of aflatoxin G1. Food Control 21(5): 719-725. DOI:10.1016/j.foodcont.2009.10.014.

Watt, J. M., Breyer-Brandwijk, M. G. B., 1962. Medicinal and poisonous plants of Eastern and Southern Africa, $2^{nd}$ edition, Edinburg London, E&S Livingston 369.

White, F., 1988. The taxonomy, ecology and chorology of African Ebenaceae II. The non-Guineo-Congolian species of *Diospyros* (Excluding sect. Royena). Bulletin du Jardin botanique National de Belgique/Bulletin van de Nationale Plantentuin van België 58 (3/4): 325-448.

Yin, H., Chen, C., Kollanoor-johny, A., Darre, M. J., 2015. Controlling *Aspergillus flavus* and *Aspergillus parasiticus* growth and aflatoxin production in poultry feed using carvacrol and trans-cinnamaldehyde and aflatoxins in feed. Poultry Science 94: 2183-2190. DOI: 10.3382/ps/pev207.

Yu, J., Chang P., Ehrlich, K. C., Cary, J. W., Bhatnagar, D., Cleveland, T. E., . . . Bennett, J. W., 2004. Clustered pathway genes in aflatoxin biosynthesis. Applied and Environmental Microbiology 70(3):1253-1262. DOI: 10.1128/AEM.70.3.1253.

Zhang C. R., Dissanayake, A. A., Nair, M. G., 2015. Functional food property of honey locust (*Gleditsia triacanthos*) flowers. Journal of Functional Foods, 18: 266-274. DOI:10.1016/j.jff.2015.07.012.

Zhang C. R., Khan, W., Bakht, J., Nair, M. G., 2016. New antiinflammatory sucrose esters in the natural sticky coating of tomatillo (*Physalis philadelphica*), an important culinary fruit. Food Chemistry, 196:726-732. DOI: 10.1016/j.foodchem.2015.10.007.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:

1. A composition comprising a carrier and at least one compound of formula I:

A-linkage-B where:

A and B are bicyclic rings with 8 to 12 ring atoms, each of the A and B bicyclic rings having (i) at least three oxygen-containing substituents selected from hydroxy (—OH), oxy (═O), ether (—O—), and alkoxy (R—OH, where R is a lower alkyl), and (ii) one or two lower alkyl substituents; and linkage is a covalent bond or a lower alkylene (e.g., $-(CH_2)_n-$, where n is an integer of 1-3) bonded to the A and B bicyclic rings.

2. The composition of statement 1, where one of the A or B bicyclic rings has an ether substituent.

3. The composition of statement 1 or 2, where one of the A or B bicyclic rings has an ether substituent and the ether substituent comprises two adjacent ring atoms bonded to an oxygen atom, thereby forming a third ring joined to the A or B bicyclic ring where the third ring has three atoms, one of which is the oxygen atom, and two of which are A or B ring atoms.

4. The composition of statement 1, 2, or 3, where the compound has formula IIa or IIb:

IIa

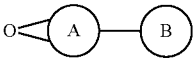, or

-continued

IIb

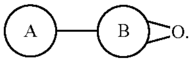

5. The composition of statement 1-3 or 4, where both of the A and B bicyclic rings have 3 or 4 oxygen-containing substituents selected from hydroxy (—OH), oxy (═O), ether (—O—), and alkoxy (R—OH, where R is a lower alkyl).

6. The composition of statement 1-4 or 5, where one of the A or B rings has three oxygen-containing substituents, while the other of the A or B rings has four oxygen-containing substituents.

7. The composition of statement 1-5 or 6, where one of the A rings has two oxy substituents.

8. The composition of statement 1-6 or 7, where one of the B rings has two oxy substituents.

9. The composition of statement 1-7 or 8, where the one or more compound(s) can have formula IIIa, IIIb, IIIc, or IIId:

IIIa

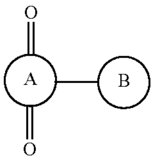

IIIb

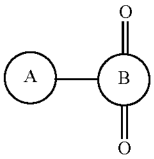

IIIc

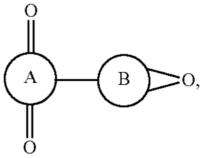 or

IIId

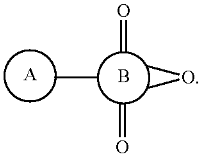

10. The composition of statement 1-8 or 9, where one of the A rings and one of the B rings has two oxy substituents.

11. The composition of statement 1-9 or 10, where the one or more compounds have formula IVa or IVb:

IVa

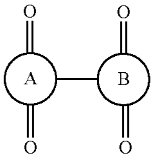 or

-continued

IVb

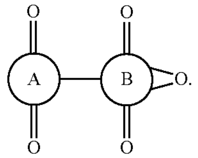

12. The composition of statement 1-10 or 11, where one of the A rings has one or two hydroxy substituents.
13. The composition of statement 1-11 or 12, where one of the B rings has one or to hydroxy substituents.
14. The composition of statement 1-12 or 13, where the A ring or the B ring has one hydroxy substituent, while the other of the A ring or the B ring has two hydroxy substituents.
15. The composition of statement 1-13 or 14, where the A or one of the rings of the A bicyclic ring is an aromatic ring.
16. The composition of statement 1-14 or 15, where one of the rings of the B bicyclic ring is an aromatic ring.
17. The composition of statement 1-15 or 16, where one of the rings of the A bicyclic ring and one of the rings of the B bicyclic ring is an aromatic ring.
18. The composition of statement 15, 16 or 17, where Aromatic rings are cyclic aromatic hydrocarbons that do not contain heteroatoms.
19. The composition of statement 15-17 or 18, where the aromatic ring is phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl.
20. The composition of statement 15-18 or 19, where the aromatic rings contain about 6 to about 14 carbons in the ring portions of the groups.
21. The composition of statement 1-19 or 20, where one of the rings of the A bicyclic ring has one or two double bonds.
22. The composition of statement 1-20 or 21, where one of the rings of the B bicyclic ring has one or two double bonds.
23. The composition of statement 1-21 or 22, where one of the rings of the A bicyclic ring and one of the rings of the B bicyclic ring has one or two double bonds.
24. The composition of statement 1-22 or 23, where the A bicyclic ring has one or two lower alkyl substituents.
25. The composition of statement 1-23 or 24, where the B bicyclic ring has one or two lower alkyl substituents. In some cases one of the rings of the A bicyclic ring has one or two lower alkyl substituents, and one of the rings of the B bicyclic ring has one or two lower alkyl substituents.
26. The composition of statement 1-24 or 25, comprising:

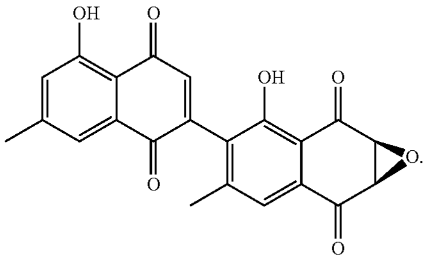

Diosquinone (DQ)

27. The composition of statement 1-24 or 26, comprising:

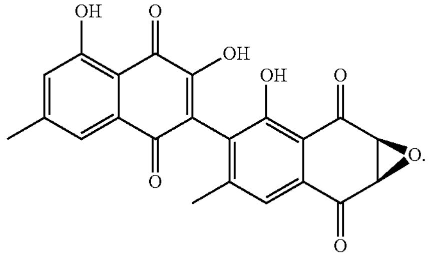

3-Hydroxydiosquinone (3HDQ)

28. The composition of statement 1-26 or 27, where the carrier is a solvent or surfactant.
29. The composition of statement 1-27 or 28, where the carrier is a solvent selected from methanol, ethanol, or propanol.
30. The composition of statement 1-28 or 29, where the carrier is an emulsifier, a dispersing agent, a thickening agent, a surfactant, a clay, a polymer, a colorant, a wetting agent, a mineral substance, a dispersant, a tackifier, a thickener, a binder, or a mixture of such carriers.
31. The composition of statement 1-29 or 30, wherein the compound(s) are at a concentration of 0.1 μg/mL to about 1000 μg/mL, or about 1 μg/mL to about 800 μg/mL, or about 3 μg/mL to about 600 μg/mL, or about 5 μg/mL to about 500 μg/mL, or about 5 μg/mL to about 300 μg/mL.
32. The composition of statement 1-30 or 31, wherein the composition comprises weight/weight concentrations of one or more compounds at about 0.1 μg/g to about 1000 μg/g or about 1 μg/g to about 800 μg/g or about 3 μg/g to about 600 μg/g or about 5 μg/g to about 500 μg/g or about 5 μg/g to about 300 μg/g.
33. The composition of statement 1-31 or 32, wherein the compound(s) are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.
34. The composition of statement 1-32 or 33, wherein the compound(s) are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm.
35. A compound of formula I:

A-linkage-B where:

A and B are bicyclic rings with 8 to 12 ring atoms, each of the A and B bicyclic rings having (i) at least three oxygen-containing substituents selected from hydroxy (—OH), oxy (=O), ether (—O—), and alkoxy (R—OH, where R is a lower alkyl), and (ii) one or two lower alkyl substituents; and linkage is a covalent bond or a lower alkylene (e.g., $-(CH_2)_n-$, where n is an integer of 1-3) bonded to the A and B bicyclic rings.

36. The compound of statement 35, where one of the A or B bicyclic rings has an ether substituent.

37. The compound of statement 35 or 36, where one of the A or B bicyclic rings has an ether substituent and the ether substituent comprises two adjacent ring atoms bonded to an oxygen atom, thereby forming a third ring joined to the A or B bicyclic ring where the third ring has three atoms, one of which is the oxygen atom, and two of which are A or B ring atoms.

38. The compound of statement 35, 36, or 37, where the compound has formula IIa or IIb:

IIa

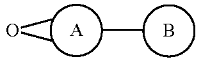

, or

IIb

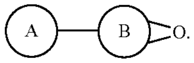

39. The compound of statement 35-37 or 38, where both of the A and B bicyclic rings have 3 or 4 oxygen-containing substituents selected from hydroxy (—OH), oxy (═O), ether (—O—), and alkoxy (R—OH, where R is a lower alkyl).

40. The compound of statement 35-38 or 39, where one of the A or B rings has three oxygen-containing substituents, while the other of the A or B rings has four oxygen-containing substituents.

41. The compound of statement 35-39 or 40, where one of the A rings has two oxy substituents.

42. The compound of statement 35-40 or 41, where one of the B rings has two oxy substituents.

43. The compound of statement 35-41 or 42, where the one or more compound(s) can have formula IIIa, IIIb, IIIc, or IIId:

IIIa

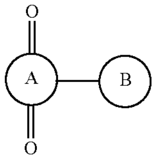

IIIb

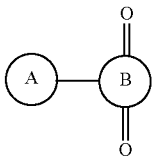

IIIc

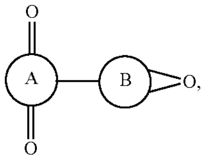

, or

IIId

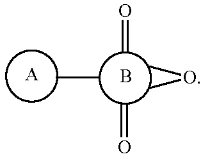

44. The compound of statement 35-42 or 43, where one of the A rings and one of the B rings has two oxy substituents.

45. The compound of statement 35-43 or 44, where the one or more compounds have formula IVa or IVb:

IVa

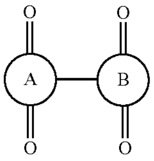

or

IVb

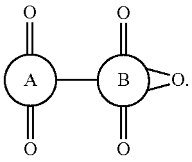

46. The compound of statement 35-44 or 45, where one of the A rings has one or two hydroxy substituents.

47. The compound of statement 35-45 or 46, where one of the B rings has one or to hydroxy substituents.

48. The compound of statement 35-46 or 47, where the A ring or the B ring has one hydroxy substituent, while the other of the A ring or the B ring has two hydroxy substituents.

49. The compound of statement 35-47 or 48, where the A or one of the rings of the A bicyclic ring is an aromatic ring.

50. The compound of statement 35-48 or 49, where one of the rings of the B bicyclic ring is an aromatic ring.

51. The compound of statement 35-49 or 50, where one of the rings of the A bicyclic ring and one of the rings of the B bicyclic ring is an aromatic ring.

52. The compound of statement 49, 50 or 51, where the aromatic ring is a cyclic aromatic hydrocarbon that does not contain heteroatoms.

53. The compound of statement 49-51 or 52, where the aromatic ring is phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl.

54. The compound of statement 49-52 or 53, where the aromatic rings contain about 6 to about 14 carbons in the ring portions of the groups.

55. The compound of statement 35-19 or 54, where one of the rings of the A bicyclic ring has one or two double bonds.

56. The compound of statement 35-54 or 55, where one of the rings of the B bicyclic ring has one or two double bonds.

57. The compound of statement 35-56 or 56, where one of the rings of the A bicyclic ring and one of the rings of the B bicyclic ring has one or two double bonds.

58. The compound of statement 35-22 or 57, where the A bicyclic ring has one or two lower alkyl substituents.

59. The compound of statement 35-57 or 58, where the B bicyclic ring has one or two lower alkyl substituents. In some cases one of the rings of the A bicyclic ring has one or two lower alkyl substituents, and one of the rings of the B bicyclic ring has one or two lower alkyl substituents.

60. The compound of statement 35-58 or 59, comprising:

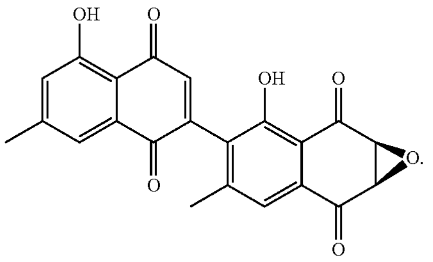

Diosquinone (DQ)

61. The compound of statement 35-58 or 59, comprising:

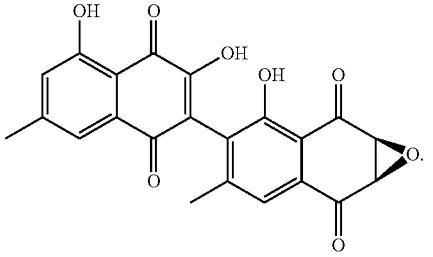

3-Hydroxydiosquinone (3HDQ)

62. A method comprising applying the composition of statement 1-33 or 34, or the compound of 35-60 or 61 to one or more plants, one or more plant seeds, one or more plant products, one or more structures, one or more laundry rooms, one or more bathrooms, one or more bedrooms, one or more closets, one or more basements, one or more attics, one or more kitchens, one or more cabinets, one or more animal pens, one or more storage areas, one or more silos, one or more grain bins, one or more building sidings, one or more decks, one or more boat surfaces, or a combination thereof.
63. The method of statement 62, wherein the plant products are animal feed.
64. The method of statement 62 or 63, wherein the plant products are human food.
65. The method of statement 62, 63 or 64, wherein the plants comprise grain-producing plants, nut-producing plants, vegetable-producing plants, fruit-producing plants, starch-producing plants, fiber-producing plants, fodder-producing plants, or a combination thereof.
66. The method of statement 62-64 or 65, wherein the plant products comprise grains, nuts, vegetables, fruits, starch, fibers, flour, fodder, leaves, stock, seeds, oil, or a combination thereof.
67. The method of statement 62-65 or 66, wherein the plant products are almonds, barley, betel nuts, brazil nuts, cashews, chestnuts, coconut, coffee, corn, flour, hazelnuts, macadamia nuts, oats, pecans, peanuts, pine nuts, pistachios, rice, rye, sesame seeds, soybean, spices, walnuts, wheat, or combinations thereof.
68. The method of statement 62-66 or 67, wherein the my cotoxin content in plants or plant products is reduced by spraying a composition onto the plants or plant products.
69. The method of statement 62-67 or 68, wherein the my cotoxin content in plants or plant products is reduced without inhibiting the growth of the fungi that synthesizes the mycotoxin.
70. The method of statement 62-68 or 69, wherein the my cotoxin content in plants or plant products is reduced by about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%.
71. The method of statement 62-69 or 70, wherein the my cotoxin content in plants or plant products is reduced to less than 50 ppm, less than 25 ppm, less than 20 ppm, less than 15 ppm, less than 10 ppm, or less than 5 ppm.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a compound," "a nucleic acid" or "a promoter" includes a plurality of such compounds, nucleic acids or promoters (for example, a solution of compounds or nucleic acids, or a series of promoters), and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method comprising applying a composition comprising a carrier and at least one compound of formula IIIa, IIIb, IIIc, or IIId:

IIIa

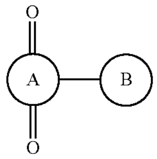

IIIb

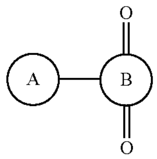

IIIc

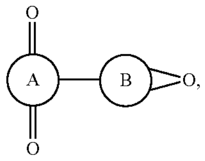

or

IIId

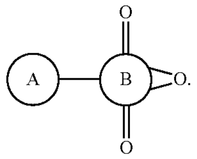

where:

A and B are bicyclic rings with 8 to 12 ring atoms, each of the A and B bicyclic rings having (i) at least three oxygen-containing substituents selected from hydroxy (—OH), oxy (═O), ether (—O—), and alkoxy (—OR, where R is a lower alkyl), and (ii) one or two lower alkyl substituents; and to one or more plants, one or more plant seeds, one or more plant products, one or more structures, one or more laundry rooms, one or more bathrooms, one or more bedrooms, one or more closets, one or more basements, one or more attics, one or more kitchens, one or more cabinets, one or more animal pens, one or more storage areas, one or more silos, one or more grain bins, one or more building sidings, one or more decks, one or more boat surfaces, or a combination thereof;

to inhibit biosynthesis of mycotoxins and fungal sporulation where so applied.

2. The method of claim 1, wherein the plant products are animal feed.

3. The method of claim 1, wherein the plant products are human food.

4. The method of claim 1, wherein the plants comprise grain-producing plants, nut-producing plants, vegetable-producing plants, fruit-producing plants, starch-producing plants, fiber-producing plants, fodder-producing plants, grains, nuts, vegetables, fruits, starch, fibers, flour, fodder, leaves, stock, seeds, oil, or a combination thereof.

5. The method of claim 1, wherein the plant products are almonds, barley, betel nuts, brazil nuts, cashews, chestnuts, coconut, coffee, corn, flour, hazelnuts, macadamia nuts, oats, pecans, peanuts, pine nuts, pistachios, rice, rye, sesame seeds, soybean, spices, walnuts, wheat, or combinations thereof.

6. The method of claim 1, wherein the mycotoxin content in plants or plant products is reduced by spraying a composition onto the plants or plant products.

7. The method of claim 1, where one of the A or B bicyclic rings has an ether substituent and the ether substituent comprises two adjacent A or B ring atoms bonded to an oxygen atom, thereby forming a third ring joined to the A or B bicyclic ring, where the third ring has three atoms, one of which is the oxygen atom, and two of which are A or B ring atoms.

8. The method of claim 1, where each of the A and B bicyclic rings has 2-4 oxygen-containing substituents selected from hydroxy (—OH), oxy (═O), ether (—O—), and alkoxy (—OR, where R is a lower alkyl).

9. The method of claim 1, where one of the A or B rings has three oxygen-containing substituents, while the other of the A or B rings has four oxygen-containing substituents.

10. The method of claim 1, where one of the A or B rings has two oxy substituents.

11. The method of claim 1, where one of the A rings and one of the B rings has two oxy substituents.

12. The method of claim 1, where one or more compounds have formula IVa or IVb:

IVa

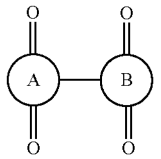

or

IVb

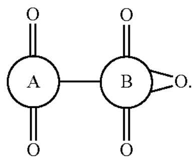

13. The method of claim 1, where one or more the A or B rings has one or two hydroxy substituents.

14. The method of claim 1, where the A ring or the B ring has one hydroxy substituent, while the other of the A ring or the B ring has two hydroxy substituents.

15. The method of claim 1, where the at least one of the A and/or B bicyclic rings is an aromatic ring with about 6 to about 14 carbons.

16. The method of claim 1, where the aromatic ring does not contain heteroatoms.

17. The method of claim 1, where the aromatic ring is phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl.

18. The method of claim 1, where at least one of the rings of the A and/or B bicyclic rings has one or two double bonds.

19. The method of claim 1, where at least one or the A and/or B bicyclic rings has one or two lower alkyl substituents.

20. The method of claim 1, wherein the composition comprises:

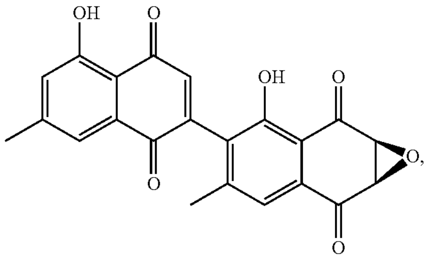

Diosquinone (DQ)

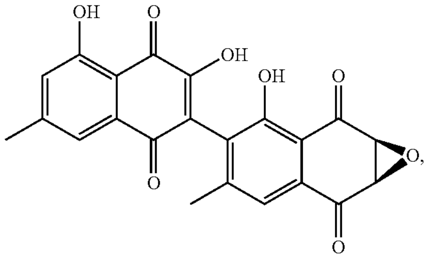

3-Hydroxydiosquinone (3HDQ)

or a combination thereof.

21. The method of claim 1, where the carrier is a solvent or surfactant.

22. The method of claim 1, where the carrier is a solvent selected from methanol, ethanol, or propanol.

23. The method of claim 1, where the carrier is an emulsifier, a dispersing agent, a thickening agent, a surfactant, a clay, a polymer, a colorant, a wetting agent, a mineral substance, a dispersant, a tackifier, a thickener, a binder, or a mixture of such carriers.

24. The method of claim 1, wherein the compound(s) are at a concentration of 0.1 μg/mL to about 1000 μg/mL, or about 1 μg/mL to about 800 μg/mL, or about 3 μg/mL to about 600 μg/mL, or about 5 μg/mL to about 500 μg/mL, or about 5 μg/mL to about 300 μg/mL.

25. The method of claim 1, wherein the composition comprises weight/weight concentrations of one or more compounds at about 0.1 μg/g to about 1000 μg/g, or about 1 μg/g to about 800 μg/g, or about 3 μg/g to about 600 μg/g, or about 5 μg/g to about 500 μg/g, or about 5 μg/g to about 300 μg/g.

26. The method of claim 1, wherein the compound(s) are at a concentration of about 0.1 ppm to 500 ppm, or about 1 ppm to 400 ppm, or about 2 ppm to 300 ppm, or about 5 ppm to 250 ppm, or about 10 ppm to 150 ppm, or about 12 ppm to 100 ppm, or about 15 to 50 ppm, or about 20 ppm to 35 ppm, or about 25 ppm.

27. The method of claim 20, wherein the diosquinone (DQ) or 3-hydroxydiosquinone (3HDQ) is at a concentration of 0.1 μg/mL to about 1000 μg/mL.

* * * * *